US006074638A

United States Patent [19]
Anderson et al.

[11] Patent Number: 6,074,638
[45] Date of Patent: Jun. 13, 2000

[54] COMPOSITION AND METHOD FOR INHIBITING PLANT DISEASE

[75] Inventors: Neil A. Anderson; Daqun Liu, both of St. Paul; Linda L. Kinkel, Forest Lake; Janet L. Schottel, Roseville, all of Minn.

[73] Assignee: Regents of the University of Minnesota, Minneapolis, Minn.

[21] Appl. No.: 08/640,749

[22] PCT Filed: May 13, 1994

[86] PCT No.: PCT/US94/05456

§ 371 Date: May 6, 1996

§ 102(e) Date: May 6, 1996

[87] PCT Pub. No.: WO94/27443

PCT Pub. Date: Dec. 8, 1994

Related U.S. Application Data

[63] Continuation-in-part of application No. 08/069,136, May 28, 1993, abandoned.

[51] Int. Cl.$^7$ .............................. A01N 63/00; C12N 1/20; A61F 35/74
[52] U.S. Cl. .................... 424/93.43; 47/58.1; 435/253.5; 435/886
[58] Field of Search ........................ 435/253.5, 886–906; 424/93.43; 47/58, 58.1

[56] References Cited

U.S. PATENT DOCUMENTS

| | | |
|---|---|---|
| 4,595,589 | 6/1986 | Tahvonen . |
| 4,849,008 | 7/1989 | Schroth et al. . |
| 4,855,230 | 8/1989 | Lindow . |

FOREIGN PATENT DOCUMENTS

| | | |
|---|---|---|
| 0408811 | 1/1991 | European Pat. Off. . |

OTHER PUBLICATIONS

Fan, T.X. et al. Microbiology, China vol. 9, No. 4, p. 153–155 (Abstract only), 1982.

Cullen et al., "Biological Control of Leaf Damage in Plants", *TIBTECH*, pp. 115–119 (May 1986).

Davison, "Plant Beneficial Bacteria", *Bio/Technology*, 6, 282–286 (Mar. 1988).

Keinath et al., "Population Dynamics of *Streptomyces scabies* and Other Actinomycetes as Related to Common Scab of Potato", *Phytopathology*, 79, 681–687 (1989).

Labeda et al., "DNA Relatedness among Strains of Sweet Potato Pathogen *Streptomyces ipomoea* (Person and Martin 1940) Waksman and Henrici 1948", *Applied and Environmental Microbiology*, 58(2), 532–535 (1992).

Watson et al., *Recombinant DNA*, second ed., by W. H. Freeman and Company, New York, pp. 89–90 and 293–312 (1992).

Adams et al., "Studies on the Lenticel Development, Surface Microflora and Infection by Common Scab (*Streptomyces scabies*) of Potato Tubers Growing in Wet and Dry Soils", *Ann. Appl. Biol.*, 90:335–343 (1978).

Archuleta et al., "The Cause of Deep–Pitted Scab of Potatoes", *Amer. Potato J.*, 58:385–392 (1981).

Beadle et al., "Heterocaryosis in Neurospora Crassa", *Genetics*, 29:291–308 (1944).

Bergey's *Manual of Determinative Bacteriology* (8th edition), "Part 17: Actinomycetes and Related Organisms", The Williams and Wilkins Co., Baltimore, MD, pp. 750–829 (1974).

Bibb et al., "Physical and Genetical Characterisation of a Second Sex Factor, SCP2, for *Streptomyces coelicolor* A3(2)", *Mol. Gen. Genet.*, 154:155–156 (1977).

Bibb et al., "Genetic Studies of the Fertility Plasmid SCP2 and its SCP2* Variants in *Streptomyces coelicolor* A3 (2)", *J. Gen. Microbiol.*, 126:427–442 (1981).

Bradley et al., "Heterokaryosis in Streptomyces", *J. Bacteriol.*, 72:219–225 (1956).

Bradley et al., "Compatibility System Controlling Heterokaryon Formation in *Streptomyces coelicolor*", *Proceedings for the Society for Experimental Biology and Medicine*, 99:476–478 (1958).

Chater and Merrick, "Chapter 6: Streptomycetes", *Studies in Microbiology*. vol. 1: *Developmental Biology of Prokaryotes*, pp. 93–114, J.H. Parish, ed., University of California Press, Berkeley, CA (1979).

Davis et al., "Effects of Gypsum, Sulfur, Terraclor and Terraclor Super–X for Potato Scab Control", *Americ. Potato J.*, 51:35–43 (1974).

Elesaway et al., "Isolation and Characterization of *Streptomyces Scabies* Strains from Scab Lesions of Potato Tubers, Designation of the Neotype Strain of *Streptomyces Scabies*", *ACTA Microbiol. Acad. Sci. Hung.*, 26:311–20 (1979).

Erikson, "Loss of Aerial Mycelium and Other Changes in Streptomycetes Development Due to Physical Variations of Cultural Conditions", *J. Gen Microbiol.*, 13:136–148 (1955).

Gordon et al., "A Piecemeal Description of *Steptomyces griseus* (Krainsky) Waksman and Henrici", *J. Gen. Microbiol.*, 50:223–233 (1968).

(List continued on next page.)

*Primary Examiner*—Mary E. Mosher
*Attorney, Agent, or Firm*—Merchant & Gould P.C.

[57] ABSTRACT

The present invention is directed to methods and compositions for biological control of plant diseases using suppressive avirulent strains of Streptomyces spp. to control disease on a vegetable or other susceptible crop. The method includes applying one or more naturally occurring, suppressive avirulent strains of Streptonmces spp. to the crop to inhibit the growth of *Streptomyces scabies* or other plant pathogenic organisms that cause scab, wilt, or seedling blight disease. Preferably, at least two suppressive avirulent strains of Streptomyces spp. are applied to reduce the change of resistance from occurring. The suppressive avirulent strains ame compatible and will grow in the presence of one another and, when combined with the pathogenic organism, at least one of the suppressive avirulent strains preferably substantially outgrows the pathogen.

14 Claims, 5 Drawing Sheets

OTHER PUBLICATIONS

Gregory, "Hyphal Anastomosis and Cytological Aspects of *Streptomyces Scabies*", *Can. J. Microbiol.*, 2:649–655 (1956).

Harrison, "Potato Russet Scab, its Cause and Factors Affecting its Development", *Amer. Potato J.*, 39:368–387 (1962).

Hayashida et al., "Production of Potato Common Scab–antigonistic Biofertilizer from Swine Feces with *Streptomyces albidoflavus*", *Agric. Biol. Chem.*, 52(10) :2397–2402 (1988).

Hayashida et al., "Control of Potato Common Scab with Antibiotic Biofertilizer Produced from Swine Feces Containing *Streptomyces albidoflavus* CH–33", *Agric. Biol. Chem.*, 53(2) :349–354 (1989).

Holliday, "A New Method for the Identification of Biochemical Mutants of Micro–organisms", *Nature*, 178:987 (1956).

Hooker, "Bacteria in Potatoes that Appear Healthy", *Compendium of Potato Disease*, pp. 33–34, American Phytopathological Society, St. Paul, MN (1990).

Hopwood et al., *Genetic Manipulation of Streptomyces. A Laboratory Manual* (The John Innes Foundation, 1985).

Hopwood et al., "Linkage and the Mechanism of Recombination in *Streptomyces coelicolor*", *Ann. NY Acad. Sci.*, 81:887–898 (1959).

Hopwood et al., "Heterozygous clones in *Streptomyces coelicolor*", *J. Gen. Microbiol*, 30:249–260 (1963).

Jones, "The Histogeny of Potato Scab", *Ann. App. Biol.*, 18:313–333 (1931).

Keinath et al., "Effects of Inoculum Density and Cultivar Resistance on Common Scab of Potato and Population Dynamics of *Streptomyces scabies*", *Phytopathology*, 79:681–687 (1991).

Keinath et al., "Population Dynamics of *Streptomyces scabies* and Other Actinomyctes as Related to Common Scab of Potato", *Amer. Potato J.*, 68:515–524 (1989).

Kerr, "Biological Control of Crown Gall Through Production of Agrocin 84", *Plant Disease*, 64:24–30 (1980).

King et al., "Correlation of Phytotoxin Production with Pathogenicity of *Streptomyces scabies* Isolates from Scab Infected Potato Tubers", *Amer. Potato J.*, 68:675–680 (1991).

Kuhlman et al., "Vegetative Compatibility and Hypovirulence Conversion Among Naturally Occurring Isolates of *Cryphonectria parasitica*", *Phytopathology*, 74:659–664 (1984).

Lambert et al., "*Streptomyces scabies* sp. nov., nom. rev.", *Int. J. Systematic Bact.* 39:387–392 (1989).

Lambert et al., "Relationship of Calcium to Potato Scab", *Phypathology*, 81:632–636 (1991).

Lapwood et al., "Mechanisms of Control of Common Scab by Irrigation", *American Phytopathology Society*, at pp. 123–129 (1975).

Lauer, "Tubers from Leaf–Bud Cuttings: A Tool for Potato Seed Certification and Breeding Programs", *Amer. Potato J.*, 54:457–464 (1977).

Lawrence et al., "Induction of Common Scab Symptoms in Aseptically Cultured Potato Tubers by the Vivotoxin, Thaxtomin", *Phytopathology*, 80(7):606–608 (1990).

Lederberg et al., "Replica Plating and Indirect Selection of Bacterial Mutants", *J. Bacteriol.*, 63:399–406 (1952).

Lorang, "Heterokaryosis and Inhibitory Reactions Among Isolates of *Streptomyces scabies* Causing Scab on Potato", Masters thesis, University of Minnesota (1988).

Lorang, "Inhibitory Reactions and Vegetative Compatibility", *Phytopathology*, 78:1579, Abstract No. 528 (1988).

Manzer et al., "A New Potato Scab Problem in Maine", *LSA Experimental Station Technical Bulletin*, 85 (1976).

McQueen et al., "Inhibitory Reactions between Natural Isolates of *Streptomyces*", *J. Gen Microbiol.*, 126:427–442 (1981).

Menzies, "Occurrence and Transfer of a Biological Factor in Soil that Suppresses Potato Scab", *Phytopathology*, 49:648–653 (1959).

Menzies, "Factors Affecting Plant Pathogen Population in Soil", *Root Diseases and Soil–Borne Pathogens*, 2nd International Symposium on Factors Determining the Behavior of Plant Pathogens in Soil held at Imperial College, London (1968) University of California Press.

Millard et al., "A Study of Twenty–Four Strains of Actinomyces and their Relation to Types of Common Scab of Potato", *Ann. App. Biol.*, 13:580–644 (1926).

Nuget, "Soil Treatments with PCNB (Terraclor) for Control of Potato Scab", *Plant Disease Reporter*, 40:428 (1956).

Okanishi et al., "Formation and Reversion of Streptomycetes Protoplasts: Cultural Condition and Morphological Study", *J. Gen. Microbiol.*, 80:389–400 (1974).

Parmeter et al., "Anastomosis Grouping Among Isolates of Thanatephorus cucumeris", *Phytopathology*, 59:1270–1278, (1969).

Polsinelli et al., "Genetic Recombination in Crosses Between *Streptomyces aureofaciens* and *Streptomyces rimosus*", *J. Bacteriology*, 91:63–68 (1966).

Rouatt et al., "The Effect of the Incorporation of Certain Cover Crops on the Microbiological Balance of Potato Scab Infested Soil", *Can. J. Research*, 28:140–152 (1950).

Schall, "Variation and Physiologic Specialization in The Common Scab Fungus (Antinomyces Scab Fungus (Antinomyces Scabies)", *J. Agr. Res.*, 69:169–196 (1944).

Schneider, *Suppressive Soils and Plant Disease*, American Phytopathology Society, St. Paul, MN, at p. 55 (1982).

Schroth et al., "Chapter 2: Behavior of Plant Pathogenic Bacteria in Rhizosphere and Non–Rhizophere Soils", *Ecology of Root Pathogens*, Elsevier Scientific Publishing Co., NY, at pp. 105–138 (1979).

Sermonti et al., "Genetic Recombination in *Streptomyces*", *Nature*, 176:121 (1955).

Sermonti et al., "New Approach to the Genetics of *Streptomyces coelicolor*", *J. Bacteriol.*, 91:384–392 (1966).

Shirling et al., "Cooperative Description of Type Strains of *Streptomyces*", *Int. J. Syst. Bacteriol.*, 22, 265–394 (1972).

Stonifer et al., "Mutagenic DNA Repair in *Streptomyces*", *Proc. Natl. Acad. Sci.*, 82:1180–1183 (1985).

Tanii et al., "Chapter 11: Biological Control of Scab, Black Scurf and Soft Rot of Potato by Seed Tuber Bacterization", *Biological Control of Soil–Borne Plant Pathogens*, Hornby, ed., C.A.B. International, at pp. 143–164 (1990).

Thaxter, "Report of the Mycologist", *Agric. Expt. Sta. Rept.*, 81:95 (1890).

Vidaver et al., "Bacteriocins of the Phytopathogens *Pseudomonas syringae*, *P. glycinea*, and *P. phaseolicola*", *Can J. Microbiol.*, 18, 705–713 (1972).

Waksman et al., "The Nomenclature and Classification of the Actinomycetes", *J. Bacteriol.*, 46:337–341 (1948).

Weinhold et al., "Selective Inhibition of the Potato Scab Pathogen by Antagonistic Bacteria and Substrate Influence on Antibiotic Production", *Plant and Soil*, 28(1):12–24 (1968).

Weinhold, "Significance of Populations of Major Plant Pathogens in Soil: Bacteria Including *Streptomyces*", in T.A. Tousson et al. (Ed.) *Root Diseases and Soil Borne Pathogens*, University of Calif. Press, Berkely and Los Angeles (1970).

Bibb et al., "Excision of Chromosomal DNA Sequences from *Streptomyces coelicolor* forms a Novel Family of Plasmids Detectable in *Streptomyces lividans*", *Mol. Gen. Genet.*, 184:230–240 (1981).

Corbaz, "Etude des streptomycetes provoquant la gale commune de la pomme de terre", *Phytopathologische Zeitschrift*, 51:351–360 (1964).

COMPOSITION AND METHOD FOR INHIBITING PLANT DISEASE

CROSS REFERENCE TO RELATED APPLICATION

This application is a continuation-in-part of application Ser. No. 08/069,136, filed May 28, 1993, abandoned.

STATEMENT REGARDING FEDERALLY SPONSORED RESEARCH

The invention described herein was made with the assistance of the U.S. Department of Agriculture under USDA Grant No. 91-34103-5960. The Government has certain rights in the invention.

BACKGROUND OF THE INVENTION

Scab disease of potatoes (*Solanum tuberosum*) is caused by several species of Streptomyces. The pathogen was first isolated in 1890 in the state of Connecticut and named *Oospora scabies* based on its melanin production and gray spores borne in spiral chains. Thaxter, *Aqric. Expt. Sta. Rept.*, 81:95 (1890). The organism was later renamed as *Streptomyces scabies*. Waksman et al., *J. Bacteriol.*, 46:337–341 (1948). Taxonomy of the organism has changed significantly over the years as different isolates of Streptomyces causing scab disease on potatoes have been given different names.

*S. scabies* was eventually reevaluated and the original description of the organism was changed to include smooth spores and use of all ISP sugars. Elesaway et al., *ACTA Microbiol. Acad. Sci. Hung.*, 26:311–20 (1979). At present, the taxonomy of *S. scabies* is based on morphological and biochemical characteristics. The confusion over Streptomyces taxonomy may be attributed to the organism's ability to produce sectors readily in culture and extreme sensitivity to physical variations of cultural conditions. Erikson, *J. Gen Microbiol.*, 13:136–148 (1955).

A number of different strains causing potato scab in the eastern United States and Canada were isolated, determined to be the same species, and grouped as *Streptomyces scabies*. Lambert et al., *Intl. J. Systematic Bact.* 39:387–392 (1989). Data indicated that *S. scabies* formed a homogeneous group characterized by smooth gray spores borne in spiral chains, melanin production, and utilization of all ISP sugars. It was thus proposed to revive the name *S. scabies* for the group of organisms which caused common scab of potato. At present, the species *S. scabies* is not listed in Bergey's *Manual of Determinative Bacteriology* (8th edition), Buchanan et al., Williams and Wilkins Co., Baltimore, Md. (1974).

Besides *S. scabies*, scab diseases on potato tubers are caused by other species of Streptomyces, as for example, *S. acidiscabies*, and additional less virulent isolates of *S. griseus*, *S. olivaceous*, *S. aureofaciens*, *S. flaveolus*. Corbaz, *Phytopathol.*, 51:351–360 (1964); Gordon et al., *J. Gen. Microbiol.*, 50:223–233 (1968); and Hutter, *Systematic der Streptomyceten*, Karger, Basel (1967); Archuleta et al., *Amer. Potato J.*, 58:385–392 (1981); Millard et al., *Ann. App. Biol.*, 8:560–644 (1926).

Crops other than potatoes, as for example, radish, beet, carrot, rutabaga, parsnip, turnip, and the like, are susceptible to scab diseases. Scab disease is a major production problem that affects grade quality, but has a relatively small effect on total yield of tubers or storing ability (Hooker, *Compendium of Potato Disease*, pages 33–34, American Phytopathological Society, St. Paul, Minn. (1990)).

Four different types of scab lesions have been observed on infected tuber surfaces. Lesions on potato tubers range from small raised scab tissue around lenticels to large, deep pits (Schroth et al., *Ecology of Root Pathogens*, pp. 129–138 (1979); Millard et al., *Ann. App. Biol.*, 13:580–644 (1926); Jones, *Ann. App. Biol.*, 18:313–333 (1931) 1941; and Schall, *J. Agr. Res.*, 69:169–196 (1944)). Russet scab lesions are formed in highly alkaline soil by an undescribed species of Streptomyces (Harrison, *Amer. Potato J.*, 39:368–387 (1962)). A recent paper, Faucher et al., *Plant Dis.*, 77:1217–1220 (1993), indicates russet scab in eastern Canada is caused by *Streptomyces aureofaciens*. Lesions from "acid scab" isolates are caused by *Streptomyces acidiscabies*. Manzer et al., LSA *Experimental Station Technical Bulletin*, 85 (1976); Lambert and Loria, *Intl. J. Systematical Bacteriology*, 39:387–392 (1989).

Streptomyces spp. are aerobic, gram-positive, soil-inhabiting, filamentous bacteria. The Streptomyces are different from most prokaryotes because they produce coherent, nonfragmenting colonies and undergo differentiation during colony development producing hyphae and spores. Chater and Merrick, *Studies in Microbiology*. Vol 1: *Developmental Biology of Prokaryotes*, pages 93–114, J. H. Parish, ed., University of California Press, Berkeley, Calif. (1979). It has been suggested the Streptomyces occupy an evolutionary position intermediate between eubacteria and lower fungi because of their filamentous growth habit, production of aerial spores, presence of reiterated DNA, and DNA repair mechanisms. Stonisfer et al., *Proc. Natl. Acad. Sci.*, 82:1180–1183 (1985).

Heterokaryosis and a compatibility system controlling heterokaryon formation were demonstrated in *S. griseus* and *S. cyaneus*. Bradley et al., *J. Bacteriol.*, 72:235–241 (1956); Bradley et al., *Proceedings for the Society for Experimental Biology and Medicine*, 99:476–478 (1958). Hyphal anastomosis of *S. scabies* has been studied from a cytological perspective. Gregory, *Can. J. Microbiol.*, 2:649–655 (1956). Vegetative compatibility with respect to heterokaryon formation by pairing N-methyl-N'-nitro-N-nitrosoguanidine (NTG) generated auxotrophic mutant strains of Streptomyces spp. Lorang, "Heterokaryosis and Inhibitory Reactions Among Isolates of *Streptomyces scabies* Causing Scab on Potato", unpublished Masters thesis, University of Minnesota (1988). Heterokaryons were formed between isolates causing various common scab lesions. In some plant pathogenic fungi, determination of vegetative compatibility groups is useful since they are linked to symptom development and host specificities. Parmeter et al., *Phytopatholovy*, 59:1270–1278, (1969).

Another study described the inhibitory reactions among paired isolates of Streptomyces spp. from potato scab lesions. McQueen et al., *J. Gen Microbiol.*, 126:427–442 (1981). In that study, plasmid DNA was found in four isolates. Further studies by Lorang (1988) showed that some inhibitory reactions were due to physical contact resembling the lethal zygosis-like reaction and others to antibiotic production. Lorang, "Heterokaryosis and Inhibitory Reactions Among Isolates of *Streptomyces scabies* Causing Scab on Potato," Masters thesis, University of Minnesota (1988). Streptomyces plasmids, such as SCP1, SCP2, and SCP2*, increased chromosomal recombination and have been physically characterized. Bibb et al., *Mol. Gen. Genet.*, 154:155–156 (1977). It was shown that the isolates with these plasmids inhibited growth of plasmid-minus isolates of Streptomyces spp. and caused the lethal zygosis-reaction. Bibb et al., *J. Gen. Microbiol.*, 126:427–442 (1981).

Some important aspects of pathogenesis by *S. scabies* have been elucidated by Lawrence et al., *Phytopathology*, 80(7):606–608 (1990). Two compounds, thaxtomins A and B, were found to be responsible for formation of symptoms typical of the common scab disease. These compounds were identified as 4-nitroindol-3-yl containing 2,5-dioxopiperazines and were obtained from cell-free extracts of scab lesions of field-grown and cultural tubers. These results were confirmed by Babcock, Eckwall and Schottel who also found that thaxtomins A and B were formed in a synthetic culture medium. Babcock et al., *J. Gen. Microbiol.*, 139:1579–1586 (1993). It has been demonstrated a positive correlation between the pathogenicity of 28 *S. scabies* isolates and their ability to produce thaxtomin A. King et al., *Amer. Potato J.*, 68:675–680 (1991)

Also associated with potato scab is the natural decline of the disease in soils repeatedly grown to potatoes for many years. Schneider, *Suppressive Soils and Plant Disease*, American Phytopathology Society, St. Paul, 88 pp. (1982). It was demonstrated that a biological factor was responsible for scab decline in these disease conducive soils. Application of 1% suppressive soil plus 1% alfalfa meal into disease conducive soils controlled the scab disease. Menzies, *Phytopathology*, 49:648–653 (1959).

In an attempt to identify the cause of scab suppression, Lorang isolated several Streptomyces isolates which produced antibiotics against isolates and reduced the number of scab lesions on radish roots in a greenhouse test and on potato tubers grown in a field test. Lorang, "Heterokaryosis and Inhibitory Reactions Among Isolates of *Streptomyces scabies* Causing Scab on Potato", Masters thesis, University of Minnesota (1988). It has also been reported that an antibiotic biofertilizer (swine feces) contained *Streptomyces albidoflavus* strain CH-33 that controlled the potato common scab disease. Hayashida et al., *Agric. Biol. Chem.*, 52(10):2397–2402 (1988); Hayashida et al., *Agric. Biol. Chem.*, 53(2):349–354 (1989). Various species of bacteria have been used in a process called "potato seed tuber bacterization" in which a 30% disease reduction was claimed. Tanii et al., *Biological Control of Soil-Borne Plant Pathogens*, Hornby, ed., C.A.B. International (1990). It was also reported that potato scab disease could be controlled by increasing soil acidity and application of fungicides to the soil. Davis et al., *Americ. Potato J.*, 51:35–43 (1974); Nuget, *Plant Disease Reporter*, 40:428 (1956).

Crop rotation is a major means of minimizing scab. Scab has also been reported to be suppressed by incorporation of green manures that enhance microbial antagonists of the scab organisms, by excess irrigation practices during tuber formation, by chemical control using gypsum, sulfur, and PCNB (pentachloronitro benzene), or by soil fumigation. Rouatt et al., *Can. J. Research*, 28:140–152 (1950); Weinhold et al., *Plant and Soil*, 28(1):12–24 (1968); Lapwood, et al., *American Phytopatholocy Society*, at pages 123–129 (1975). It has been reported that scab incidence was correlated with soil pH, but was not correlated with calcium concentration in soil, healthy tuber periderm, or medulla tissue. Lambert and Manzer, *Phytopathology*, 81:632–636 (1991). In that study, scab lesion diameter was inversely correlated with tuber magnesium and manganese concentration.

The use of scab resistant potato cultivars is another method of disease control. In a study on population dynamics, it was indicated that the total population of Actinomycetes and *S. scabies* were greater on the tuber surface of the susceptible cultivar Chippewa than the resistant cultivar Superior, but soil and rhizosphere populations of these bacteria did not differ between cultivars. Keinath et al., *Amer. Potato J.*, 68:515–524 (1989). In general, scab severity increased linearly with an increase in $\log_{10}$ of *S. scabies* inoculum (Keinath and Loria, *Phytopathology*, 79:681–687 (1991)).

The need to reduce our dependence on chemicals to control plant disease is recognized widely. The use of chemicals is expensive, and one traditional chemical approach using sulfur to maintain low soil pH limits the crops that can be grown in rotation with potatoes.

Attempts have been made to develop biological controls for plant diseases, but only a few methods have been successful. For example, *A. radiobacter* strain 84 which produces agrocin 84 was developed as a biological control against crown gall (*Agrobacterium tumefaciens*). Kerr, *Plant Disease*, 64:24–30 (1980). Another example of a biocontrol mechanism is the control of the American chestnut blight caused by *Cryphonectria parasitica* by use of vegetatively compatible strains of the pathogen into which double stranded RNA has been transferred to make them hypo. Kuhlman et al., *Phytopathology*, 74:659–664 (1984).

Therefore, an object of the invention is to develop a biological control for plant diseases such as scab disease in potatoes and other susceptible crops. Another object is to develop a method for inhibiting scab caused by Streptomyces spp. Yet another object is to develop a biological control for diseases caused by Fusarium, Rhizoctonia, Verticillium, Pythium, Clavibacter, and other like soil-borne plant pathogens.

SUMMARY OF THE INVENTION

These and other objects are achieved by the present invention which is directed to methods and compositions for biological control and inhibition of plant diseases by inhibiting the growth of *Streptomyces scabies* and other plant pathogenic organisms that cause diseases on a susceptible crop. According to the invention, one or more naturally occurring suppressive species of Streptomyces is used to inhibit formation of scab lesions and/or to effectively control other plant pathogens on vegetables and other crops.

The invention provides avirulent strains (i.e., isolates) of Streptomyces spp. which are capable of suppressing the growth of pathogenic *Streptomyces scabies* and other plant pathogenic organisms including, for example, *Verticillium dahliae, Fusarium solani, Rhizoctonia solani*, and the like, which form wilt, root and stolon diseases on potatoes and other susceptible crops. As used herein, the term "suppressive avirulent strain" means a strain of Streptomyces spp. which is capable of inhibiting (i.e., retarding or eliminating) the growth of one or more species and/or strains of a plant pathogenic organism and preferably can substantially outgrow the strains on a susceptible crop such that the size and/or number of lesions on the crop are eliminated or substantially reduced. Examples of avirulent strains of Streptomyces spp. provided according to the invention include, Streptomyces spp. strain 15 (ATCC No. 55414), Streptomyces spp. strain 32 (ATCC No. 55416), and Streptomyces spp. strain 93 (ATCC No. 55415).

The suppressive avirulent strains of Streptomyces spp. can preferably substantially out-grow the pathogenic strain preferably within about 1–5 days following application on the susceptible crop, more preferably within about 1–3 days. The suppressive avirulent strains preferably persist in the soil and/or rhizosphere for at least one growing season and preferably over several growing seasons. After a single inoculation into the soil, seed or plant, a preferred suppressive avirulent Streptomyces can persist for at least about 1 to 6 years in the soil and/or rhizosphere.

It is also preferred that the suppressive avirulent strain is capable of producing at least one growth-inhibiting amount of a substance, as for example, an antibiotic, against the pathogenic organism. An antibiotic preparation that includes at least one antibiotic can be obtained from cell culture medium of suppressive Streptomyces spp. such as PonSSII, strain 15, strain 93, strain 32 and mixtures thereof. The antibiotic preparation can be used to form a biopesticidal composition with or without a suppressive Streptomyces spp. The antibiotic preparation is useful in methods of inhibiting growth of plant pathogens and controlling plant diseases on crops.

A method of the invention comprises applying an effective amount of at least one suppressive avirulent strain of Streptomyces spp. to a susceptible crop such as a vegetable, as for example, a potato, beet, radish, and the like, to inhibit the growth of one or more different species and/or strains of plant pathogenic organisms, as for example, *Streptomyces scabies, Verticillium dahliae, Fusarium solani, Rhizoctonia solani*, and the like. The avirulent suppressive Streptomyces strain can be applied as a single application or as multiple applications over several growing seasons. A method of the invention also includes combining application of an avirulent suppressive Streptomyces strain with traditional crop management techniques such as crop rotation. While not meant to limit the invention, the suppressive avirulent strain of Streptomyces spp. can inhibit the strain of pathogenic organism by substantially out-growing the strain on the susceptible crop and/or by production of an antibiotic that inhibits the growth of the strain.

In a preferred method according to the invention, a combination of two or more suppressive avirulent strains of Streptomyces spp. are applied to the susceptible crop. The combination of at least two suppressive avirulent strains of Streptomyces spp. reduces the development of resistant forms of the pathogen on the crop. Preferably, two or more of the suppressive avirulent strains of the combination are capable of substantially out-growing the pathogenic strains on the susceptible crop. The suppressive avirulent strains of the combination are compatible with each other in that one avirulent strain does not inhibit the growth of another avirulent strain. It is preferred that at least two of the avirulent strains of the combination are capable of co-growth when combined together on the susceptible crop. It is further preferred that at least two of the avirulent strains of the combination do not produce inhibitory compounds against each other.

A composition of the invention is biopesticidal and includes at least one suppressive avirulent strain of Streptomyces spp. in combination with a physiologically-acceptable carrier, as for example, an aqueous medium such as water, a growth media, fertilizer, soil, vermiculite, clay, algal compounds such as alginate, and other like granular materials. A composition comprises the suppressive avirulent strain of Streptomyces spp. in an amount effective to inhibit the growth of a pathogenic strain of *Streptomyces scabies* and/or other plant pathogenic organism on a vegetable or other susceptible crop.

A preferred biopesticidal composition comprises a combination of at least two different suppressive avirulent strains of Streptomyces spp., preferably three strains, preferably four strains. At least one, preferably at least two, of the suppressive avirulent strains can substantially outgrow the pathogenic strain. The suppressive avirulent strains of Streptomyces spp. combined in the composition are compatible with each other in that one strain does not inhibit the growth of another strain of the combination. A preferred composition comprises the combination of two or more of strains of Streptomyces spp. selected from strain 15 (ATCC No. 55414), Streptomyces spp. strain 32 (ATCC No. 55416), and Streptomyces strain 93 (ATCC No. 55415).

The invention also provides methods of identifying suppressive Streptomyces spp. from pure culture and biological samples. The methods of identification include analyzing cellular fatty acids, identifying a mutant suppressive strain having an identifiable marker gene, using polymerase chain reaction and using antibodies that are specific for a particular Streptomyces spp.

The invention advantageously provides a method and composition for the natural biological control of scab and other soil-borne diseases on crops in agricultural end-use settings. The invention also provides a method to minimize the use of pesticides to control plant disease.

| | | |
|---|---|---|
| aa | Streptomyces strain 93-161L | |
| ab | Streptomyces strain 93-231L | |
| ac | Streptomyces strain RB4-93-19L | (Washington isolate) |
| ad | Streptomyces strain 93-35L | (Washington isolate) |
| ae | Streptomyces strain 93-30L | (Washington isolate) |
| af | Streptomyces strain 93-56L | (Washington isolate) |
| ag | Streptomyces strain 93-41L | (Washington isolate) |
| ah | Streptomyces strain 93-10L | |
| ai | Streptomyces strain 93-23L | |
| aj | Streptomyces strain 93-96L | |
| ak | Streptomyces strain 93-8L | |
| al | Streptomyces strain 93-2L | |
| am | Streptomyces strain 93-63L | (Washington isolate) |
| an | Streptomyces strain 93-3L | |
| ao | Streptomyces strain RB4-6L | |
| ap | Streptomyces strain 11L | |
| aq | Streptomyces strain 38L | |
| ar | Streptomyces strain 93-151L | |

Figure 2:
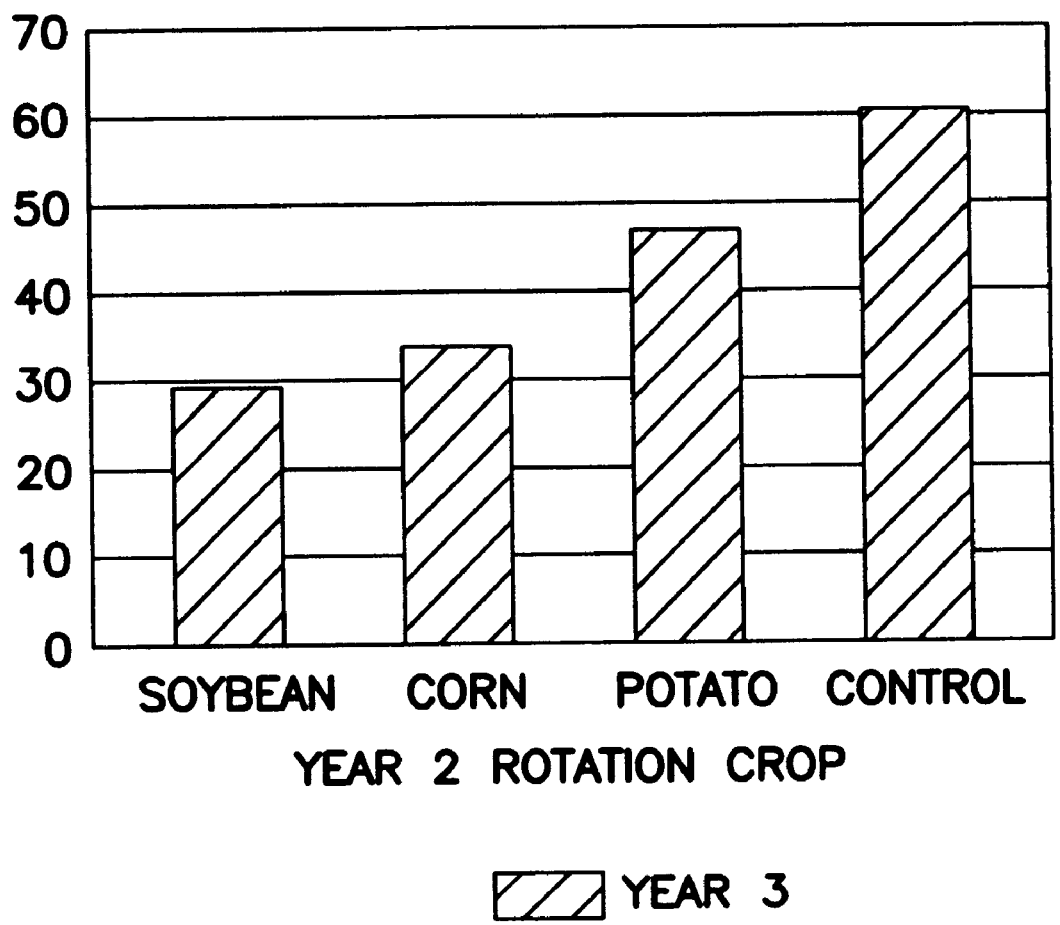

FIG. 2 is a graph showing disease control with a single inoculation of a suppressive Streptomyces spp. over several growing seasons combined with crop rotation.

Figure 3:
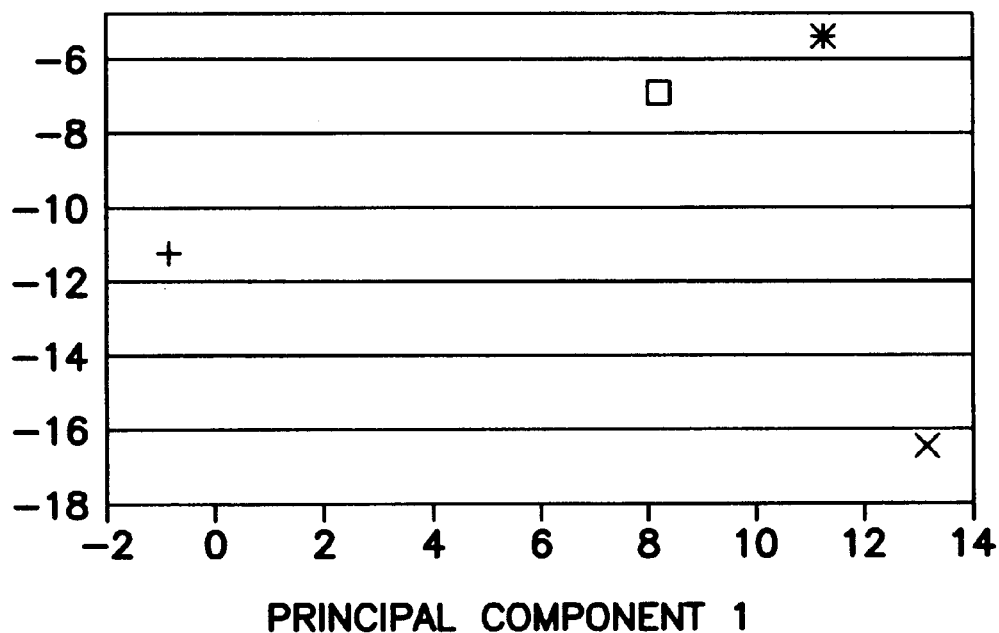

FIG. 3 is principle component analysis of cellular fatty acids of suppressive Streptomyces species as follows:

| | |
|---|---|
| . | Strain 32 |
| □ | PonR |
| + | Strain 93 |
| X | Strain 15 |
| * | PonSSII |

Figure 4:
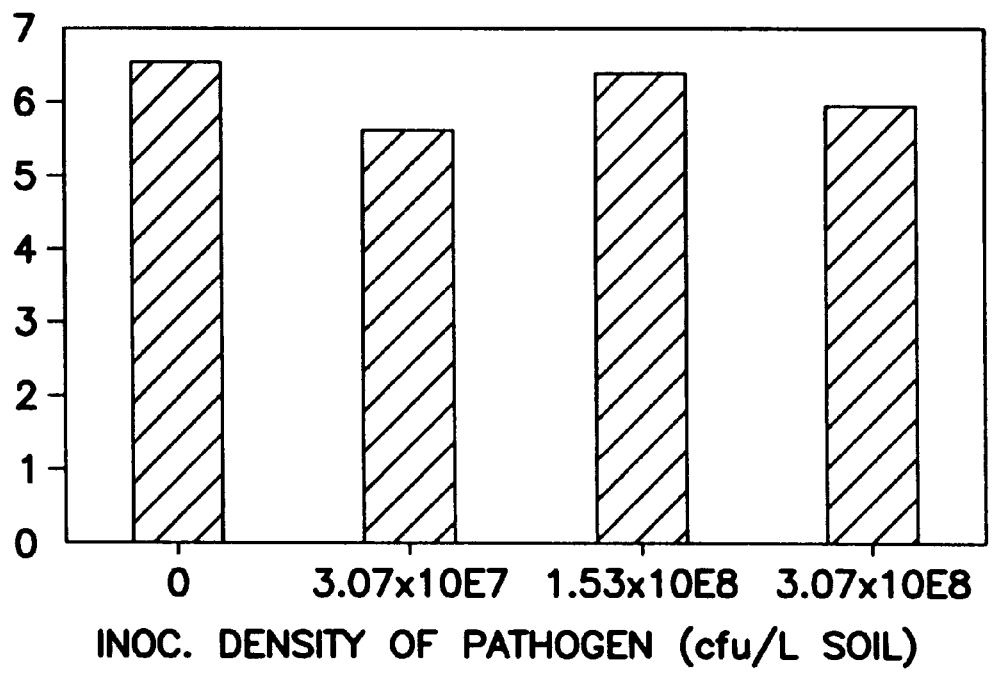

FIG. 4 is a graph showing the relationship between pathogen inoculum density and root population when coinoculated with suppressive strain 93.

Figure 5:
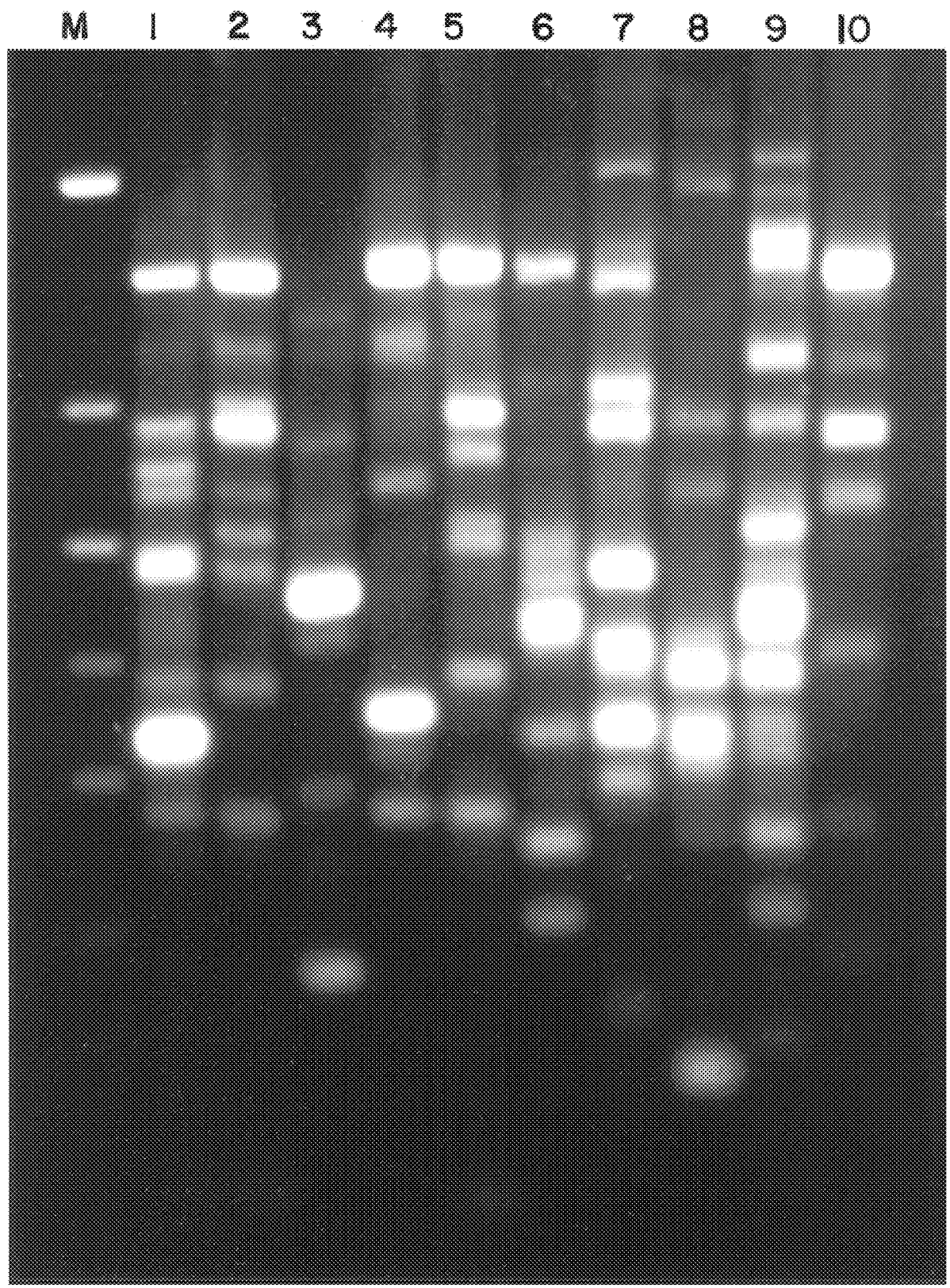

FIG. 5 is PCR amplification of Streptomyces genomic DNA. The amplified DNA fragments were visualized by gel electrophoresis on 1.5% agarose next to molecular length markers (M).

1. *S. scabies* strain RB4
2. *S. scabies* strain 87
3. S. spp. strain Crystal
4. *S. scabies* strain RB5
5. *S. scabies* strain PonC 6. S. spp. strain 93

7. *S. scabies* strain PonR

8. S. diastatochromogenes strain PonSSII

9. S. spp. strain 32

10. S. spp. strain 15

Molecular weight markers are in column designated M and are 1444 bp, 955 bp, 736 bp, 585 bp and 476 bp.

DETAILED DESCRIPTION OF THE INVENTION

A. Biopesticidal Compositions and Methods of Using Biopesticidal Compositions A method of the invention provides a natural means of biologically controlling a plant disease, such as scab disease, on a susceptible crop. According to the method, an effective growth-inhibiting amount of a suppressive avirulent strain of Streptomyces spp. is applied to the susceptible crop to inhibit the growth of one or more species and/or strains of a pathogenic plant microorganism. The application of a suppressive avirulent strain of Streptomyces spp. can also provide for growth enhancement either directly or indirectly. Growth enhancement can be observed by a significant increase in yield and/or quality of the plant product. While not meant to limit the invention in any way, it is believed that growth enhancement can occur indirectly by inhibiting the growth of deleterious pathogens in the soil.

The suppressive Streptomyces spp. can be obtained from lenticels or scab lesions on a plant or more preferably from suppressive soil. When the suppressive Streptomyces are isolated from suppressive soil, preferably they can be obtained from suppressive soil from Grand Rapids, Minn. and from suppressive soil from Washington State (Menzies). The suppressive isolates are selected for the ability to inhibit the growth of pathogens, preferably to outgrow a pathogen and preferably to co-grow with other suppressive strains. The soil suppressive isolates are selected to be superior with respect to inhibition of plant pathogens compared with the lenticel or scab isolates. The soil isolates are also preferred because of the ability to persist in acid or alkaline soil conditions.

A suppressive avirulent strain of Streptomyces spp. is applied to the crop in an amount effective to inhibit the growth of a pathogenic strain of a plant pathogenic organism. The suppressive avirulent strain of Streptomyces spp. is preferably capable of substantially outgrowing and/or inhibiting the growth of the pathogenic strain.

The composition of the invention is biopesticidal and includes at least one suppressive avirulent strain of Streptomyces spp. in an amount effective to inhibit the growth of a strain of *Streptomyces scabies* and/or other plant pathogenic microorganism on a vegetable or other crop, in combination with a physiologically-acceptable carrier. The suppressive avirulent strain of Streptomyces spp. is preferably capable of outgrowing and/or inhibiting the growth of a strain of a plant pathogenic microorganism including, as for example, *S. scabies, Verticillium dahliae, Verticillium alboatrum, Fusarium solani, Rhizoctonia solani, Cylindrocladium floridanum, Clavibacter michiganense* subsp. *sepidonicum, Phytophthora megasperma* pv. *glycinea* race 1, Pythium spp., Septoria spp., Sclerotinia and other like pathogens and diseases associated with these pathogens. These plant pathogens are associated with diseases such as wilts, root rot, seedling blights, and damping off. For example *V. dahliae* causes wilt and *Rhizoctonia solani* causes root rot and seedling blight. The plants affected by these pathogens preferably include vegetables, soybeans, wheat, alfalfa, sugar beets, hybrid poplars and corn.

Examples of crops susceptible to seedling blight diseases include alfalfa, field beans, soy beans, corn, sugar beets; pine, spruce and conifer nurseries; bedding plants and greenhouses; vegetables such as potatoes and tomatoes; turf and turf grasses; wheat and other small grains such as oats, barley and the like. When the biopesticidal composition is applied to inhibit seedling blight diseases, it is preferably applied as a seed treatment or to plants or to soil in liquid or granular form. Seed treatment formulations are commercially available. Examples of useful suppressive avirulent strains of Streptomyces spp. according to the invention include Streptomyces spp. strain 15 (ATCC No. 55414), strain 32 (ATCC No. 55416), and strain 93 (ATCC No. 55415). These exemplary strains were deposited with the American Type Culture Collection (ATCC), 10801 University Boulevard, Manassas, Va. 20110-2209, on Apr. 6, 1993.

A biopesticidal composition including at least one suppressive Streptomyces spp. can be used in control of *S. scabies* and scab diseases. Vegetables which may be treated according to the method include, for example, a potato, beet, radish, carrot, rutabaga, parsnip, turnip, and other like vegetables susceptible to a scab disease.

The suppressive avirulent strain of Streptomyces spp. may be applied, for example, to vegetable seeds, to the soil in close proximity to the plant and seeds, or by trickle-drip irrigation, and the like. Seeds can be treated by dipping into a slurry of suppressive strain of Streptomyces or by mixing with a granular formation of the suppressive Streptomyces strain or strains. The suppressive avirulent strain may be applied for example, as a solution which is sprayed on or about the crop or seeds, as a granular material admixed with a fertilizer and added to the soil, and other like application methods to bring the avirulent strain in contact with the plant. For example, a furrow may be opened in the soil and a liquid or granular composition containing the avirulent strain may be placed into the furrow such that the avirulent strain comes into contact with the seed portion of the vegetable. In a preferred method, a solution or granular product containing at least one, preferably two, suppressive avirulent strains of Streptomyces spp. is applied to the soil or seeds and/or directly onto the crop.

For control of scab disease, the biopesticidal composition is preferably applied to the soil or as a seed treatment, or both at planting, and is preferably applied in successive growing seasons. The application of a biopesticidal composition can also be combined with traditional crop management techniques including crop rotation. For example, the suppressive strain can be applied to a crop such as potatoes, to the soil, or to the seeds in the first year. In subsequent growing seasons such as 1 to 3 years, a different crop can be grown in the same plot of land with or without additional applications of the biopesticidal composition. When the susceptible crop is replanted in the same plot of land, after one or more growing seasons, the crop, seed, or soil can be optionally reinoculated with the biopesticidal composition to achieve a significant inhibition of scab disease.

The suppressive Streptomyces strain can preferably persist in the soil, in the seed population, or in the rhizosphere for a period of time sufficient to inhibit disease development with or without multiple applications. The period of time will depend, in part, on the disease and microorganism causing the disease. For inhibition of scab disease, preferably suppressive Streptomyces strains that can persist after one application for about 2 weeks to about 4 years, more preferably about 12 weeks to about 3 years are selected. The suppressive Streptomyces strains can be detected in the soil, seed population, or rhizosphere using a variety of methods including by culture, analysis of cellular fatty acids, detection of an identifiable marker gene, by an antibody specific for a suppressive Streptomyces strain, or by polymerase chain reaction.

A preferred composition comprises a combination of two or more suppressive Streptomyces strains, preferably three strains, preferably four strains. According to the invention, at least one of the suppressive avirulent strains of the combination is capable of substantially out-growing the pathogenic organism on the susceptible crop or other nutrient medium. The suppressive avirulent strains are compatible with each other when combined together on a susceptible crop, such as a vegetable, or other nutrient medium, in that one suppressive Streptomyces strain does not inhibit the growth of another suppressive Streptomyces strain of the combination. It is preferred that the avirulent strains of the combination are capable of co-growth or enhanced growth, when combined together on the susceptible crop and/or nutrient growth medium. A preferred combination of Streptomyces spp. strains is the combination of strain 32 (ATCC No. 55416); with strain 93 (ATCC No. 55415). A strain of Streptomyces spp. may be combined with another strain in a ratio from about 99:1 to about 1:99, preferably about 1:3 to about 3:1, preferably about a 1:1 ratio.

The suppressive avirulent strain of Streptomyces spp. is combined with a carrier which is non-toxic and physiologically-compatible with the a bacterial strain and the vegetable or other crop being treated. An aqueous suspension of the avirulent strain may be combined with the carrier in a liquid form, or the suspension may be freeze-dried, granulated and then combined with the carrier. Suitable carriers include, for example, a liquid medium such as water, a nutrient broth medium such as oatmeal broth, and the like; a dry and/or particulate medium such as alginate or other algae-derived substance, soil, clay particles, vermiculite, peat, and other like granular materials; and other like carriers.

A liquid composition preferably includes about $10^4$–$10^{10}$ colony forming units (CFU) or "spores" of the suppressive avirulent strain per milliliter, preferably about $10^5$–$10^9$ CFU/ml, preferably about $10^6$–$10^8$ CFU/ml. It is preferred that a non-liquid or solid form of the composition includes about $10^5$–$10^{12}$ CFU of the suppressive avirulent strain per gram, preferably about $10^7$–$10^{10}$ CFU/gm, preferably about $10^8$–$10^9$ CFU/gm.

An effective amount of the composition is applied to a crop in an agricultural setting to provide the suppressive avirulent strain in an amount effective to out-grow the strain within about 1–5 days following application, preferably within about 1–3 days. Preferably, a solid form of the composition is applied to a crop at about 1–100 lb per acre, preferably about 10–50 lb/acre, preferably about 20–30 lbs/acre, and a liquid composition is applied at about 5–40 gallons per acre, preferably about 10–30 gallons per acre, preferably about 15–20 gallons per acre.

B. Generation of Mutants of Suppressive Streptomyces Strains

The invention also provides for mutants of the suppressive Streptomyces strains. Mutants of the Streptomyces strains preferably have an enhanced ability to inhibit plant pathogenic microorganisms and/or include an identifiable marker gene. An enhanced ability to inhibit plant pathogenic microorganisms includes those mutants that inhibit at least one more plant pathogenic microorganism than the parent wild-type strain or produce more of an antibiotic that inhibits at least one plant pathogenic microorganism than the parent wild-type strain.

Mutants of the suppressive strains can be isolated and generated using standard methods. To isolate naturally occurring random mutants, single spores can be screened for the ability to inhibit at least one plant pathogenic microorganism and/or for an identifiable marker gene such as an antibiotic resistance gene. Naturally arising mutants can be identified and amplified. Alternatively, mutants of the suppressive Streptomyces strains can be generated by exposure to mutagenic agents such as N-methyl-N-nitro-N-nitrosoguanidine or ethylenemethylsulfate or irradiation or the like. Mutants can also be generated by using transposable elements such as Tn5096, Tn5098, and Tn5099 as described by Hahn et al., *J. Bact.*, 173:5573 (1991); and McKenney et al., *J. Bact.*, 173:5578 (1991).

A screening method can be used to identify and isolate single spore mutants of suppressive Streptomyces strains as follows. Single colonies resulting from a dilution series of each suppressive strain can be grown for 5–7 days on oatmeal agar. Single colonies are screened for antibiotic production using a plate assay. One or more mutant colonies can be spotted on a lawn of a pathogenic microorganism along with the parent wild type strains. Strains that preferably produce about 20 to 1000% more antibiotic than the parental wild type strain as measured by a zone of inhibition are selected.

Optionally, colonies are numbered and a sample from each colony is transferred to individual wells of a multiwell plate filled with oatmeal agar. Optionally, the oatmeal agar can include an antibiotic so that antibiotic resistant mutants can be identified and selected, or a different detectable agent can be included that can indicate the presence of an identifiable marker gene. Multiwell colonies can be grown for 5–7 days. After the 5–7 day incubation, the individual wells can also be analyzed for production of an antibiotic that inhibits the growth of a plant pathogen. Multiwell colonies can be overlaid with sterile water agar. A suspension of a plant pathogenic strain can be applied to the water agar surface. Growth of the pathogen in the presence of each of the single spore mutant suppressive isolates can be compared to the level of growth in the presence of the parent suppressive strains. Mutants that are enhanced or are deficient in their inhibition of a plant pathogen can be subcultured and the enhanced or decreased production of an antibiotic can be confirmed using the plate method as shown in Example 2. Using chemical mutagenesis, a mutagenesis frequency of about $1\times10^{-4}$ can be expected.

Obtaining a mutant with a identifiable marker gene can be useful to identify the suppressive Streptomyces strains added to the soil and/or seeds. Preferably, a mutant with an identifiable marker gene can inhibit the same plant pathogenic microorganisms as the parent wild-type microorganism. A mutant with an identifiable marker gene can also be useful to identify and isolate mutants having an enhanced inhibition of plant pathogens. An identifiable marker gene is a gene that is preferably unique to a suppressive Streptomyces strain and is not normally found in saprophytic or strain of Streptomyces. The identifiable marker gene functions to produce a gene product that allows the identification and/or selection of the suppressive Streptomyces strains from other Streptomyces spp. Identifiable marker genes include genes encoding antibiotic resistance such as rifampicin resistance, a gene encoding β-galactosidase, luciferase, Xyl-E gene, and the like. The identifiable marker genes can be either selected for in a naturally occurring population of suppressive Streptomyces strain, or be induced by mutagenesis, or can be introduced using a transposable element. The preferred identifiable marker gene is rifampicin resistance.

Obtaining a mutant with enhanced inhibition of plant pathogens can be useful as a more efficient and/or effective biocontrol agent of plant diseases. Preferably, a mutant inhibits the growth of at least one plant pathogen the same as the parent wild-type strain and produces as much antibiotic as the parent wild-type strain. A mutant with enhanced inhibition can also inhibit the growth of more plant pathogens than the parent wild-type strain, preferably 1–20 more plant pathogens can be inhibited by a mutant suppressive Streptomyces strain. A mutant with enhanced inhibition can also produce more antibiotic as measured by the plate overlay method described in Example 2 as compared to the parent wild-type strain. Preferably, the mutant produces about 25% to 1000% more than the amount observed produced by the parent wild-type strain. Some mutants can both inhibit the growth of more plant pathogens and produce more antibiotic than the parent wild-type strain.

Optionally, the mutant can be additionally screened for the ability to outgrow a pathogenic microorganism such as *S. scabies* and/or co-grow with other suppressive Streptomyces spp. In a preferred version, a mutant is obtained that has enhanced antibiotic production as compared with the parental wild type strain, has an identifiable marker gene, can outgrow a pathogenic microorganism, and can cogrow with other suppressive Streptomyces spp.

In a preferred version, a liquid culture of a suppressive Streptomyces strain such as strain 15, 32 or 93 is exposed to a mutagenic agent such as N-methyl-N-nitro-N-nitrosoguanidine for 2 hours at 30° C. Surviving colonies are then plated on oatmeal agar and incubated for 5–7 days. Surviving colonies can then be assayed by the plate overlay antibiotic assays or transferred to individual wells of a multiwell plate that have been filled with oatmeal agar. Multiwell colonies can be grown for 5–7 days, after which they are overlaid with sterile water agar. A suspension of at least one pathogenic strain will be applied to each water agar surface. Growth of the pathogen in the presence of each of the single spore suppressive isolates can be evaluated and compared with the level of the growth occurring in the presence of the suppressive strain parent after 5 days. Mutants that are enhanced in their inhibition of the pathogen can be identified and subcultured from the original dilution plates. Mutants can then be checked for their antibiotic activity a second time using the assay as described in Example 2. Mutants that have an enhanced production of an antibiotic of at least about 25% can then be identified and selected. Optionally, the mutants generated can be screened for inhibition of several different plant pathogens using the multiwell plate assay and a mutant that inhibits the growth of at least one more plant pathogen than the parent wild-type strain can be identified and selected.

C. Isolation of Antibiotics Produced by Suppressive Streptomyces spp.

Suppressive Streptomyces spp. produce at least one antibiotic that inhibits the growth of virulent *S. scabies*. A suppressive Streptomyces strain can also produce at least one antibiotic that inhibits virulent *S. scabies* and at least one other plant pathogen such as *Verticillium dahliae, Verticillium albo-atrum, Fusarium solani, Rhizoctonia solani, Cylindrocladium floridanum, Clavibacter michiganense* subsp. *sepidonicum, Phytophthora megasperma* pv. *glycinea* race 1, Pythium spp., Septoria spp., Sclerotinia and other like pathogens. An antibiotic that inhibits the growth of virulent *S. scabies* can be isolated from cultures of suppressive Streptomyces strains such as PonSSII, using chromatographic methods known to those of skill in the art. The antibiotics are useful to inhibit virulent *S. scabies* and other plant pathogens if applied to soil, seeds, plants, and seedlings and can be used in methods to control plant diseases.

An antibiotic isolated from a suppressive strain such as PonSSII can inhibit the growth of virulent *S. scabies* and not *Verticillium dahliae, Verticillium alboatrum, Fusarium solani, Rhizoctonia solani, Cylindrocladium floridanum, Clavibacter michiganense* subsp. *sepidonicum, Phytophthora megasperma* pv. *glycinea* race 1, Pythium spp., Septoria spp., Sclerotinia and other bacteria shown in Table XV. The antibiotic can be isolated using standard chromatographic methods as follows. An extract of a pure culture of suppressive Streptomyces strain is prepared by growing the culture to stationary phase in a liquid medium, centrifuging and filtering the supernatant through Whatman #1 paper. The filtrate is then chromatographed on an Amberlite XAD-2 (Mallinckrodt) column and eluted with increasing concentrations of MeOH in water. Fractions are analyzed for biological activity using a filter disc assay. Fractions collected at 40% methanol have biological activity for inhibition of a virulent of strain *S. scabies*, strain RB4. Fractions having biological activity are pooled and rechromatographed using C18 thin layer chromatography (TLC) with 60% $H_2O$, 40% MeOH and 0.3 M NaCl solvent. Bands having biological activity are collected and eluted using 60% MeOH, 10 mM $KH_2PO_4$. The biologically active fractions are further fractionated using cellulose TLC in 50% $CHCl_3$, 40% MeOH, and 10% $H_2O$. Bands having biological activity are pooled and separated by reverse phase HPLC. A single peak containing biological activity is obtained.

The antibiotic isolated as described above from PonSSII is resistant to proteinase K treatment, active in pH ranges of about 7 or less (i.e. about pH=4–7), and has a size less than 3000 mw as determined by size exclusion filtration. The profile of biological activity for the isolated antibiotic is shown in Example 8. The antibiotic is inhibitory against *S. scabies* isolates and not inhibitory against the bacteria shown in Table XIV.

An antibiotic that can inhibit virulent *S. scabies* as well as *Verticillium dahliae, Verticillium albo-atrum, Fusarium solani, Rhizoctonia solani, Cylindrocladium floridanum, Clavibacter michiganense* subsp. *sepidonicum, Phytophthora megasperma* pv. *glycinea* race 1, Pythium spp., Septoria spp., Sclerotinia and other like pathogens is produced by suppressive Streptomyces strains 15, 32 and 93 and can be isolated.

The antibiotic preparation isolated from suppressive Streptomyces spp. PonSSII, strain 15, strain 32, or strain 93 can be used in methods to inhibit and control plant pathogenic infections and diseases. The antibiotic can be isolated as described herein and combined with an appropriate carrier for delivery to the seed, soil or plant. The antibiotic preparation is preferably derived from more than one suppressive Streptomyces spp. and an effective amount can be applied to the seeds, soil or plant to inhibit the plant pathogen. Preferably, the antibiotic is combined in a formulation with at least one suppressive Streptomyces spp. and an appropriate carrier, as described previously.

An effective amount of the isolated antibiotic preparation can be determined using standard methods. For example, undiluted or a 1:10 dilution of the culture filtrate from strains PonSSII, 32, 15 or 93 is spotted onto a lawn of a plant pathogen such as *S. scabies* RB4 and the size of zone of inhibition is measured. A zone of inhibition of about 1.8 cm in size in the linear range of activity is assigned a 1 unit value. After each subsequent purification step, the remaining activity can be determined by measuring the zone of inhibition at a similar dilution compared with that of the starting material. The isolated antibiotic preparation will have a certain potency as defined by units of activity. Once the units of activity of the isolated preparation are known, a similar test for an appropriate dose in a field pot test can be done to determine the range of effective amount of the antibiotic preparation. The effective amount of the antibiotic preparation is that amount that inhibits incidence of the plant disease or inhibits the growth of the plant pathogen.

While not meant to limit the invention in any way, it is believed that the antibiotic or antibiotics produced by suppressive Streptomyces spp. such as 15, 32 or 93 have a widespread effect on many genera within the major classes of fungi and gram positive microorganisms. For example, strains 15, 32 and 93 are capable of inhibiting the growth of *V. dahliae, V. albo-atrum*, Sclerotinia, *Septoria musiva, Fusarium solani, Rhizoctonia solani, Clavibacter michiganense, Phytophthora megasperma* p.v. *glycinea* race 1, *Pythium ultimum*, and *Pythium paroecandrum*. It is believed that this inhibition is due at least in part to one or more antibiotics and that the ability of the antibiotic to inhibit many different genera of the major classes of fungi indicates that it has widespread efficacy.

D. Methods for Identification of Suppressive Streptomyces Strains

The invention also provides for novel methods of identification of suppressive Streptomyces strains from other pathogenic and saprophytic Streptomyces spp. One method involves identifying suppressive Streptomyces spp. by cellular fatty acid profile. Another method involves identifying a suppressive Streptomyces strain by using an antibody specific for that strain. A third method involves identifying a mutant of a suppressive Streptomyces strain that has an identifiable marker gene such as rifampicin resistance. A fourth method includes identification of strains using polymerase chain reaction. The methods of the invention are useful for identification of suppressive Streptomyces spp., preferably from mixed populations of microorganisms. The identification methods can be combined with selective enrichment for Streptomyces spp. from environmental samples including enrichment media such as oatmeal agar amended with antibiotics and tyrosine.

Suppressive Streptomyces spp. can be identified and distinguished from other Streptomyces spp. including virulent *S. scabies* by analysis of the cellular fatty acid profile as detected by gas liquid chromatography using the Microbial Identification System (Microbial ID, Inc., Newark, Del.).

Isolates can be grown on oatmeal agar at 28° C. for 5–7 days followed by growth in trypticase soy broth for 72 hours. Mycelia are harvested and about 200 mg (wet weight) are processed according to standard methods. Cellular fatty acids are saponified, methylated to form fatty acid methyl esters, extracted from the aqueous phase into an organic phase, and washed. The fatty acid methyl esters are separated using a Hewlett Packard 5890A gas chromatograph and peaks are named, measured and expressed as percentages of the total fatty acid profile.

The fatty acid profile of an individual isolate is compared to a library of fatty acid profiles for suppressive strains generated with Microbial Identification Library Generation Software (MIDI, Newark, Del.). The library can be obtained from Dr. Linda Kinkel (University of Minnesota, St. Paul, Minn.). Identification and relationship of strains of Streptomyces were determined using cluster (dendrograms) and principle component analysis using the Library Software.

The method can be used to monitor the persistence of a suppressive Streptomyces strain in the field, soil, seed preparations, rhizosphere, and other like environments as a function of time. The cellular fatty acid profile can allow differentiation of suppressive Streptomyces strains and can be used to determine the portion of the suppressive Streptomyces strain as compared with a total Streptomyces spp. present in a sample.

In another method, a suppressive Streptomyces strain can be detected and identified by using an antibody specific for that Streptomyces strain. Preferably, the antibody is specific for the strain and lacks substantial crossreactivity with other strains of Streptomyces such as virulent *S. scabies* and/or saprophytic Streptomyces spp. preferably determined by ELISA or other competition assay. The steps of the method include isolating a population of Streptomyces spp., contacting the population of Streptomyces with a detectably labelled antibody specific for a suppressive Streptomyces strain to form an immune complex, and identifying the suppressive Streptomyces strain by detecting those microorganisms that have bound the detectably labelled antibody.

Optionally, a kit for the identification of suppressive Streptomyces strains can be prepared including at least one antibody specific for a suppressive Streptomyces strain. The kit can also preferably contain a standard sample of a pure culture of a suppressive Streptomyces strain to serve as a positive control. Optionally, the kit can contain an antibody specific for a suppressive Streptomyces strain that is detectably labelled or a detectably labelled second antibody specific for the antibody to the suppressive Streptomyces strain. The kit preferably includes reagents for detecting the bound antibody when necessary.

A third method of identification of a suppressive Streptomyces strain including from an environmental sample includes identifying a mutant of a suppressive strain that has an identifiable marker gene. A mutant of a suppressive strain with an identifiable marker gene can be prepared as described herein. Once the mutant strain has been selected or engineered to have the identifiable marker gene, the suppressive strain can be identified and/or selected from a mixed population of Streptomyces by detection of the gene product of the identifiable marker gene.

A fourth method of identification of suppressive Streptomyces including from an environmental sample involves the use of polymerase chain reaction. Nucleic acids from an individual isolate from tryptone broth can be isolated and mixed with at least one primer that will amplify Streptomyces nucleic acids. The primer binds to or is complementary to an evolutionarily conserved region of Streptomyces chromosome. The nucleic acids of the isolate are mixed with a primer in a standard PCR assay. The PCR products are separated and detected. Each isolate has a unique pattern of PCR products and can be identified by comparison to the patterns known for suppressive and pathogenic Streptomyces spp. A library of PCR patterns for known Streptomyces strains can be obtained from Dr. Janet Schottel (University of Minnesota, St. Paul, Minn.).

The invention will be further described by reference to the following detailed examples, wherein the methodologies are as described below. These examples are not meant to limit the scope of the invention that has been set forth in the foregoing description. Variation within the concepts of the invention are apparent to those skilled in the art. The disclosures of the cited references throughout the application are incorporated by reference herein.

EXAMPLE 1

Isolation and Characterization of Virulent and Suppressive Strains of Streptomyces Isolates of Streptomyces spp. were obtained from tubers grown in scab suppressive and disease conducive soils. The isolation yielded 93 isolates of which 24 isolates were nonpathogenic and inhibited growth of virulent *S. scabies* isolates in the laboratory and greenhouse studies, as shown below at Table I. Eighteen isolates of Streptomyces were also provided by J. Lorang, of the University of Minnesota, as listed below at Table II. Eleven isolates of *S. scabies* and two isolates of *S. acidiscabies* were provided by Dr. R. Loria of Cornell University, as listed below at Table III.

The isolates were characterized by standard methods as described by Lambert and Loria, *Int. J. Systematic Bact.* 39:387–392 (1989) and Bergey's *Manual of Determinative Bacteriology*, 8th edition, Buchanan et al., Williams and Wilkins Co., Baltimore, Md., 1246 pp. (1974). The physical and biochemical characteristics of the isolates were compared to *S. scabies* strain RL-34 (ATCC No. 49173).

Isolation of Streptomyces isolates. Scab lesions on potato tubers from suppressive and disease conducive soils were used to isolate species of Streptomyces according to the method of Harrison, *Amer. Potato J.*, 39, 368–387 (1962). In brief, about 5 mm³ of diseased tuber tissue was cut and rinsed in 1% (v/v) sodium hypochlorite solution and washed two times with sterile distilled water. The tissue was sliced into approximately 1 mm thick sections and five slices were placed on a 5% water agar plate. After 3–5 days of incubation at room temperature, aerial hyphae having Streptomyces morphology were identified with the aid of a dissecting microscope and transferred to oatmeal agar (Shirling et al., *Int. J. Syst. Bacteriol.*, 22, 265–394 (1972). Several transfers were performed as needed to obtain a pure culture. Spore suspensions were made by adding 10 ml of sterile water to 7–10 day old cultures, scraping the colony surface with a sterile loop, and filtering through sterile cotton. The resulting suspension was centrifuged at 1500 RPM for 20 minutes, and harvested spores were resuspended in 20% glycerol and stored in the freezer at −10° C.

Ninety-three Streptomyces isolates were obtained from both potato scab suppressive and disease conducive soils. The origin, original lesion type, and cultivar of breeding line from which a Streptomyces isolate was obtained are listed below in Table I.

TABLE I

| Isolate | Cultivar | Original lesion type[1] | Origin |
|---|---|---|---|
| 1 | Cobbler | S | GR[2], MN |
| 2 | Cobbler | S | GR, MN |
| 3 | Cobbler | S | GR, MN |
| 4 | Cobbler | S | GR, MN |
| 5 | Cobbler | S | GR, MN |
| 6 | Cobbler | S | GR, MN |
| 7 | Cobbler | S | GR, MN |
| 8 | Cobbler | S | GR, MN |
| 9 | Cobbler | S | GR, MN |

TABLE I-continued

| Isolate | Cultivar | Original lesion type[1] | Origin |
|---|---|---|---|
| 10 | Cobbler | S | GR, MN |
| 11 | Cobbler | S | GR, MN |
| 12 | Cobbler | S | GR, MN |
| 13 | Cobbler | S | GR, MN |
| 14 | Cobbler | R | GR, MN |
| 15 | Cobbler | S | GR, MN |
| 16 | Cobbler | R | GR, MN |
| 17 | Cobbler | S | GR, MN |
| 18 | Norchip | S | Becker, MN |
| 19 | Norchip | S | Becker, MN |
| 20 | Norchip | S | Becker, MN |
| 21 | Norchip | S | Becker, MN |
| 22 | Norchip | S | Becker, MN |
| 23 | Pontiac | S | Becker, MN |
| 24 | Pontiac | S | Becker, MN |
| 25 | Pontiac | R | Becker, MN |
| 26 | Breeding line 202 | S | GR, MN |
| 27 | Breeding line 75 | S | GR, MN |
| 28 | Breeding line 75 | S | GR, MN |
| 29 | Breeding line 98 | S | GR, MN |
| 30 | Breeding line E1 | S | GR, MN |
| 31 | Breeding line N1 | S | GR, MN |
| 32 | Breeding line N1 | S | GR, MN |
| 33 | Breeding line P1 | S | GR, MN |
| 34 | Breeding line P1 | S | GR, MN |
| 35 | Pontiac | S | GR, MN |
| 36 | Pontiac | S | GR, MN |
| 37 | Pontiac | S | GR, MN |
| 38 | Pontiac | S | GR, MN |
| 39 | Pontiac | S | GR, MN |
| 40 | Pontiac | S | GR, MN |
| 41 | Pontiac | S | GR, MN |
| 42 | Pontiac | S | GR, MN |
| 43 | Pontiac | S | GR, MN |
| 44 | Cobbler | S | GR, MN |
| 45 | Cobbler | S | GR, MN |
| 46 | Cobbler | S | GR, MN |
| 47 | Cobbler | S | GR, MN |
| 48 | Cobbler | S | GR, MN |
| 49 | Cobbler | S | GR, MN |
| 50 | Cobbler | S | GR, MN |
| 51 | N-NDT9-106811R | S | North Dakota |
| 52 | N-1382-6R | S | North Dakota |
| 53 | N-1408-8R | S | North Dakota |
| 54 | N-2224-5R | S | North Dakota |
| 55 | N-24-5R | S | North Dakota |
| 56 | N-2225-11R | S | North Dakota |
| 57 | N-N1 | S | North Dakota |
| 58 | Unknown | S | Big Lake, MN |
| 59 | Unknown | S | Big Lake, MN |
| 60 | Unknown | R | Big Lake, MN |
| 61 | Norchip | S | Becker, MN |
| 62 | N-79-1068-11R | S | North Dakota |
| 63 | Pontiac | S | GR, MN |
| 64 | Pontiac | S | Becker, MN |
| 65 | Cobbler | S | GR, MN |
| 66 | Cobbler | S | GR, MN |
| 67 | Breeding line 74 | S | GR, MN |
| 68 | Pontiac | S | GRC[3], MN |
| 69 | Cobbler | S | GRC, MN |
| 71 | Pontiac | S | Becker, MN |
| 72 | Cobbler | R | Becker, MN |
| 73 | Cobbler | R | Becker, MN |
| 74 | Cobbler | P | Becker, MN |
| 75 | Cobbler | P | Becker, MN |
| 76 | Cobbler | P | Becker, MN |
| 77 | Cobbler | C | Becker, MN |
| 78 | Pontiac | S | Becker, MN |
| 79 | Pontiac | S | Becker, MN |
| 80 | Pontiac | S | Becker, MN |
| 81 | Pontiac | S | Becker, MN |
| 82 | Pontiac | S | Becker, MN |
| 83 | Pontiac | P | Becker, MN |
| 84 | Pontiac | C | Becker, MN |
| 85 | Pontiac | C | Becker, MN |
| 86 | Pontiac | C | Becker, MN |

TABLE I-continued

| Isolate | Cultivar | Original lesion type[1] | Origin |
|---|---|---|---|
| 87 | Pontiac | C | GRC, MN |
| 88 | Pontiac | C | GRC, MN |
| 89 | Pontiac | P | GRC, MN |
| 90 | Pontiac | P | GRC, MN |
| 91 | Norchip | S | GRC, MN |
| 92 | Norchip | S | GRC, MN |
| 93 | Norchip | S | GRC, MN |

[1]S = infected lenticel; R = russet scab; C = superficial common scab; P = pit scab.
[2]GR = suppressive soil of potato scab disease plot, Grand Rapids, MN. This plot was used from 1942–1972 to screen potato germplasm for scab resistance. It was abandoned after 1972 because of disease decline.
[3]GRC = conducive soil of potato scab research plot, Grand Rapids, MN. (1973 to 1993)

Eighteen Streptomyces isolates were obtained from J. Lorang of the University of Minnesota. The cultivar, original lesion type, origin, and disease index are listed below in Table II.

TABLE II

| Isolate | Cultivar | Original lesion type[1] | Origin | Disease index[2] |
|---|---|---|---|---|
| FLII | Atlantic | U | Florida | 2/3 |
| Beet* | Garden Beet | P | Becker, MN | — |
| BC* | Cobbler | C | Becker, MN | 3/3 |
| Roy* | Russet Burbank | P | Royalton, MN | 5/4 |
| NC | Norchip | P | Becker, MN | 5/4 |
| Crys | Crystal | R | Grand Forks | 1.5/3 |
| RB2 | Russet Burbank | P | Becker, MN | 5/4 |
| RB3 | Russet Burbank | P | Becker, MN | 5/4 |
| RB3II | Russet Burbank | P | Becker, MN | 4.5/3 |
| RB4 | Russet Burbank | C | Becker, MN | 5/4 |
| RB5 | Russet Burbank | R | Becker, MN | 5/4 |
| PonP | Pontiac | P | Becker, MN | 5/4 |
| PonC | Pontiac | C | Becker, MN | 3.5/3 |
| PonR | Pontiac | R | Becker, MN | 1.5/3 |
| ME2 | Unknown | U | Maine | 0 |
| PonSSI | Pontiac | S | GR[3], MN | 1/3 |
| PonSSII | Pontiac | S | GR, MN | 1/3 |
| PonSSR | Pontiac | S | GR, MN | 0 |

[1]Lesion type designators are U-unknown, P-pit lesion, C-superficial common scab, R-russet scab, and S-lenticel of potato grown in suppressive soil.
[2]Disease index values were determined by pathogenicity tests on microtubers. The numerator represents lesion depth: 1-trace, 2-slight, 3-broken periderm, 4-pit lesion, and 5-deep pit lesion. The denominator represents area coverage: 1-trace, 2-slight, 3-medium, and 4-heavy.
[3]GR: suppressive soil at Grand Rapids.
*Pathogenicity determined on Kennebec only.

Isolates PonSSII, PonSSI, PonR, and PonSSR were considered suppressive isolates because they inhibited growth of virulent isolates of S. scabies in antibiotic assays. Isolates PonSSII and PonSSI were also able to reduce the number of scab lesions formed on radish roots in greenhouse tests and on tubers of two potato cultivars grown in the field.

Eleven isolates of Streptomyces scabies and two isolates of S. acidiscabies were obtained from Dr. R. Loria of Cornell University. The origin of these isolates is listed below in Table III.

TABLE III

| Isolate | Origin |
|---|---|
| Common scab | |
| 83-01-05 | LI, NY |
| 83-01-12 | LI, NY |
| ATCC 49173* | Upstate NY |
| 84-01-42 | Upstate NY |
| 84-01-70 | Maine |
| 84-01-232 | West Va |
| 85-01-07 | Maine |
| 86-01-40 | NJ |
| 87-01-19 | Fl |
| 88-01-06 | Hastings, Fl |
| 88-01-10 | Va |
| Acid scab | |
| 84-01-104 | Upstate NY |
| 84-01-182 | Maine |

*Type strain of Streptomyces scabies.

Taxonomy. Isolates of Streptomyces spp. were identified to species based on the method of Lambert and Loria, Intl. J. Systematical Bacteriology, 39:387–392 (1989), for identification of S. scabies, and Bergey's Manual of Determinative Bacteriology (8th edition), Buchanan et al., Williams and Wilkins Co., Baltimore, Md., 1246 pp (1974) for other Streptomyces species. The type strain of S. scabies used was RL-34 (ATCC No. 49173). The morphological and biochemical characteristics of S. scabies isolates and suppressive strains of Streptomyces spp. are shown below in Table IV.

TABLE IV

| Characteristics | ATCC 49173 | RB3II | RB4 | PonSSI | PonSSII | PonSSR | 15 | 17 | 26 | 32 | 44 | 93 |
|---|---|---|---|---|---|---|---|---|---|---|---|---|
| Spore color[1] | G | G | G | G | G | G | G | G | G | G | G | G |
| Chain morphology[2] | S | S | S | RF | RF | S | S | S | RF | RF | S | RF |
| Spore ornamentation[3] | Sm | Sm | Sm | Sm | Sm | Sm | Sm | Sm | Sm | Sm | Sm | SmSm |
| Melanin production | +[4] | + | + | + | + | − | + | + | + | + | − | + |
| Pigment on PYI[5] | + | + | + | + | + | − | + | + | + | + | − | + |
| Carbon usage | | | | | | | | | | | | |
| L-arabinose | + | + | + | + | + | + | + | + | + | +/− | + | +/− |
| D-fructose | + | + | + | + | + | + | + | + | + | +/− | + | +/− |
| D-glucose | + | + | + | + | + | + | + | + | + | + | + | + |
| D-mannitol | + | + | + | +/− | +/− | +/− | +/− | + | + | +/− | +/− | +/− |
| Raffinose | + | + | + | + | + | + | + | + | + | +/− | + | +/− |

TABLE IV-continued

| Characteristics | ATCC 49173 | RB3II | RB4 | PonSSI | PonSSII | PonSSR | 15 | 17 | 26 | 32 | 44 | 93 |
|---|---|---|---|---|---|---|---|---|---|---|---|---|
| Rhamnose | + | +/− | + | + | + | + | + | + | + | +/− | + | +/− |
| D-xylose | + | + | + | + | + | + | + | + | + | +/− | + | +/− |
| D-galaclose | + | + | + | + | + | + | + | + | + | +/− | + | +/− |
| Salicin | +/− | +/− | +/− | +/− | +/− | + | +/− | + | +/− | + | +/− | + |
| Nitrogen Usage | | | | | | | | | | | | |
| L-hydroxyproline | + | + | + | + | + | + | − | + | + | + | + | + |
| L-Methionine | + | + | + | + | − | − | − | + | + | + | + | + |
| Degradation of | | | | | | | | | | | | |
| Arbutin | + | + | + | + | + | + | + | + | + | + | + | + |
| Polygalacturanate | + | + | + | + | + | + | + | − | + | − | + | − |
| Xanthine | − | − | − | − | − | − | − | − | + | + | − | + |
| Xylan | + | + | + | − | − | + | + | + | + | − | + | − |
| Min growth pH | 4.0 | 5.0 | 5.0 | 5.0 | 5.0 | 4.5 | 4.5 | 4.5 | 4.0 | 4.5 | 4.0 | 5.0 |
| Growth with: | | | | | | | | | | | | |
| 5% NaCl | + | + | + | + | + | + | + | − | + | − | + | − |
| 6% NaCl | + | + | + | + | + | + | + | − | + | − | − | − |
| 7% NaCl | + | + | + | + | + | − | + | − | + | − | − | − |
| Tellurite (10 ug/ml) | + | + | + | + | + | − | + | − | + | + | − | + |
| Tellurite (100 ug/ml) | − | − | + | + | − | − | − | − | − | − | − | − |
| Thallium (10 ug/ml) | − | − | + | + | − | − | + | − | − | − | − | − |
| Thiallium (100 ug/ml) | − | − | − | − | − | − | − | − | − | − | − | − |
| Crystal violet (0.5 ug/ml) | − | − | + | − | + | − | + | − | − | + | − | + |
| Phenol (0.1%) | − | + | + | + | − | + | + | − | − | + | − | + |
| Penicillin (10 IU/ml) | − | − | + | + | − | − | + | − | + | + | − | + |
| Oleandomycin (25 ug/ml) | − | − | − | + | − | − | − | − | + | + | + | — |
| Oleandomycin (100 ug/ml) | − | − | − | + | − | − | − | − | − | − | − | — |
| Streptomycin (20 ug/ml) | − | − | + | − | − | − | − | − | − | − | − | — |

[1]G, gray; P, pink
[2]S, sprial; RF, rectiflexous
[3]Sm, Smooth
[4]+, positive reaction; −, negative reaction
[5]PYI, Peptone yeast extract iron agar.

EXAMPLE 2

Inhibition and Resistance of Suppressive *S. scabies* Strains Determined by Antibiotic Assays The 93 isolates obtained in Example 1 were used in antibiotic tests against the pathogenic isolate RB3II in a double layer agar method according to Vidaver et al., *Can J. Microbiol.*, 18, 705–713 (1972).

Four suppressive isolates, including PonSSII, were spot-plated (10 μl at $10^7$–$10^8$ spores/ml), at 4 spots/plate onto R2YE regeneration media and incubated at 30° C. for 3 days (Hopwood et al., *Genetic Manipulation of Streptomyces. A Laboratory Manual* (The John Innes Foundation, 1985)). These isolates were killed by inverting the plates over 3 mls of chloroform placed in a watch glass, for 1 hour. The watch glasses with chloroform were then removed and the plates left with covers ajar for minutes until all of the excess chloroform evaporated. The plates were overlaid with 15 mls of 1% water agar and inoculated with 100 μl of pathogenic isolate RB3II at a concentration of $10^7$ to $10^8$ spores/ml. The resulting plates were inverted and incubated at 30° C. for 3–5 days. Two replicate plates were made for each combination, and the average diameter of the growth inhibition zones were recorded.

The results of the antibiotic assay and pathogenicity test provided a preliminary selection of suppressive isolates producing larger inhibition zones against virulent isolate RB3II than the isolate PonSSII. The results of the antibiotic assay are shown below in Table V.

TABLE V

| Isolate | Cultivar | Original lesion type[1] | Inhibition zones[2] | Disease index[3] |
|---|---|---|---|---|
| 1 | GR, MN[4] | S | S | 2/1 |
| 2 | GR, MN | S | M | 2/1 |
| 5 | GR, MN | S | M | 1/1 |
| 6 | GR, MN | S | S | 1/1 |
| 7 | GR, MN | S | M | 1/1 |
| 15 | GR, MN | S | VS | 0/0 |
| 17 | GR, MN | S | VS | 0/0 |
| 22 | Becker, MN | S | M | 4/4 |
| 24 | Becker, MN | S | M | 2/1 |
| 26 | GR, MN | S | VS | 0/0 |
| 29 | GR, MN | S | M | 1/1 |
| 31 | GR, MN | S | S | 2/1 |
| 32 | GR, MN | S | VS | 0/0 |
| 33 | GR, MN | S | M | 2/1 |
| 34 | GR, MN | S | S | 2/2 |
| 37 | GR, MN | S | S | 2/1 |
| 38 | GR, MN | S | M | 2/1 |
| 39 | GR, MN | S | M | 2/1 |
| 44 | GR, MN | S | VS | 0/0 |
| 48 | GR, MN | S | S | 2/2 |
| 82 | Becker, MN | S | S | 5/4 |
| 90 | GRC, MN[5] | P | — | 2/2 |
| 91 | GRC, MN | S | M | 2/2 |
| 92 | GRC, MN | S | S | 2/2 |
| 93 | GRC, MN | S | VS | 0/0 |
| PonSSII | GR, MN | S | W-M | 0/0 |

TABLE V-continued

| Isolate | Cultivar | Original lesion type[1] | Inhibition zones[2] | Disease index[3] |
|---|---|---|---|---|
| PonR | Becker, MN | R | W-M | 1/3 |
| RB3II | Becker, MN | P | — | 2.5/2 |

[1]S = infected lenticel; P = pit lesion; R = russet scab.
[2]The diameter of the inhibition zones in the lawns against RB3II: W (weak) < 12 mm; M (medium) = 12–20 mm; S (strong) > 20–35 mm; and VS (very strong) > 35–55 mm.
[3]Disease index was determined by pathogenicity tests on microtubers of cv.Kennebec in greenhouse. The numerator indicates scab lesion depth: 1-trace, 2-slight, 3-broken periderm, 4-pit lesion, and 5-deep pit lesion. The denominator represents area coverage of scab disease on microtubers: 1-trace (2–5%), 2-slight (5–15%) 3-medium (15–30%); and 4-heavy (>30%).
[4]Suppressive soil of former scab disease plot at Grand Rapids, MN.
[5]Conducive soil of present scab disease plot at Grand Rapids, MN.

The results show that 24 of the 93 isolates provided better inhibition of RB3II than the suppressive isolate PonSSII, 4 isolates showed an inhibition similar to PonSSII, 7 isolates showed less inhibition than PonSSII, and 58 isolates did not exhibit any inhibition of RB3II.

Suppressive isolates 15, 17, 26, 32, 44, and 93 showed very strong suppression of the virulent isolate RB3II as evidenced by the formation of clear inhibition zones in the lines of the virulent isolate. These 6 suppressive isolates were tested against 6 other virulent isolates obtained from J. Lorang, the University of Minnesota. The suppressive isolates exhibited either very strong or strong inhibition of the virulent isolates. Isolates 15, 17, 32, and 93 showed very strong inhibition on all 6 virulent isolates. The reverse antibiotic assays were also done, that is, the 6 virulent isolates were spotted on R2YE media against the 6 suppressive isolates as lawns. No inhibition reactions were observed by any of the virulent isolates against the suppressive isolates.

EXAMPLE 3

Compatibility and Ability of Suppressive Strains to Grow in the Presence of One Another To determine growth compatibility of the isolates, 100 μl of a spore suspension of one suppressive isolate at a concentration of $10^7$ to $10^8$ spores/ml was spread in R2YE media in a petri plate. Ten μl of a spore suspension of a different suppressive isolate at this same concentration was placed in the center of the plate. Readings were recorded after 7 days of incubation at 30° C. R2YE media was used with one replicate for each combination. Twenty-suppressive isolates, including PonSSII and PonR, were co-inoculated in all possible combinations as both lawn and center isolates. None of the isolates formed inhibition zones against themselves. In the total combinations of suppressive isolates (26×26=576), 41% exhibited co-growth reactions.

The results of this analysis are summarized below Table VI.

TABLE VI[1]

| Lawn Isolate | Center Isolate | | | | | |
|---|---|---|---|---|---|---|
|  | ATCC 49173 | 15 | 32 | 93 | PonSSII | PonR |
| 7 | C | C | 11* | 13 | T | T |
| 31 | T | C | 15 | 15 | T | T |
| 32 | T | C | C | C | T | T |
| 37 | T | C | 20 | 16 | T | C |
| 93 | T | C | C | C | T | T |

[1]Reactions were designated as cogrowth (C), taking over (T), or inhibition as measured by the diameter of inhibition zone in millimeters.
*not complete inhibition Suppressive isolates 15, 32 and 93 were very strong inhibitors forming inhibition zones on all 17 virulent isolates. Suppressive isolate 15 formed inhibition zones against 18 other suppressive isolates, showed co-growth with suppressive isolates 7, 31, 32, 37 and 93, but was overgrown by isolates 91 and 92. Suppressive isolates 32 and 93 showed similar inhibition patterns in that they formed inhibition zones on 24 other suppressive isolates, co-grew with each other, and were not overgrown by any other isolate.

EXAMPLE 4

Competition with Virulent Strains: Ability of Suppressive Strains to Overgrow Virulent Strains To determine competitive ability of the isolates, 100 μl of a spore suspension of one virulent isolate at a concentration of $10^7$–$10^8$ spores/ml was spread in R2YE media in a petri plate. Ten μl of a spore suspension of a suppressive isolate at the same concentration was placed in the center of the plate. Readings were recorded after 7 days of incubation at 30° C. R2YE media was used with one replicate for each combination. Table VII, below, shows the growth inhibition by suppressive isolates 15, 17, 26, 32, 93, PonSSII, and PonR as center isolates on virulent isolates RB2, RB3, RB3II, RB4, RB5, PonP, and PonC as lawn isolates based on coplating assays on R2YE medium.

TABLE VII

| Lawn Isolate | Center Isolate | | | | | | | |
|---|---|---|---|---|---|---|---|---|
|  | 15 | 17 | 26 | 32 | 44 | 93 | PonSSII | PonR |
| RB2 | 14 mm | C | C | 30 mm | T | 30 mm | C | T |
| RB3 | 20 mm | C | C | 33 mm | T | 30 mm | C | C |
| RB3II | 24 mm | 11 mm | C | 35 mm | T | 38 mm | C | C |
| RB4 | 20 mm | C | C | 31 mm | C | 36 mm | C | C |
| RB5 | 24 mm | C | C | 31 mm | T | 38 mm | C | C |
| PonC | 23 mm | C | C | 25 mm | T | 32 mm | C | T |
| PonP | 15 mm | T | C | 25 mm | T | 32 mm | C | T |

Reactions were designated as co-growth (C), taking over (T) = completely overgrown, or by the diameter of inhibition zones measured in millimeters.

Suppressive isolates 15, 32 and 93 were very strong inhibitors, forming inhibition zones on all 7 virulent isolates. Other suppressive isolates such as 31, 91 and 92 showed strong inhibition on the virulent isolates. Isolates PonSSII and PonR, the first suppressive isolates used, showed co-growth with most of the virulent isolates grown as lawns on R2YE media.

The six superior suppressive isolates 15, 17, 26, 32, 44, and 93 as based on antibiotic assays against RB3II, plus PonSSII and PonR as center isolates were tested against 7 virulent isolates obtained from J. Lorang. These co-plating tests indicate that isolates I5, 32 and 93 inhibited growth of the virulent isolates, but isolates 17, 26, 44, PonSSII, and PonR did not. The exception was isolate 17 which showed weak inhibition on the growth of RB3II (see above at Table VII).

The reverse tests indicated that isolates 32 and 93 as lawn isolates, took over all the virulent isolates, and isolate 15 took over all the virulent isolates except for isolate RB4. However, isolates 17, 26, 44, PonSSII and PonR as lawn isolates mostly showed co-growth with the virulent isolates, as shown below in Table VIII which shows the growth inhibition by suppressive isolates 15, 17, 26, 32, 44, 93, PonSSII, and PonR as lawn isolates on virulent isolates RB2, RB3, RB3II, RB4, RB5, PonP, and PonC as center isolates based on co-plating assays on R2YE medium.

TABLE VIII

| Lawn Isolate | Center Isolate | | | | | | |
|---|---|---|---|---|---|---|---|
| | RB2 | RB3 | RB3II | RB4 | RB5 | PonC | PonP |
| 15 | T | T | T | C | T | T | T |
| 17 | C | 17 | C | C | C | 15 | C |
| 26 | C | C | C | C | C | C | C |
| 32 | T | T | T | T | T | T | T |
| 44 | C | C | C | C | C | C | C |
| 93 | T | T | T | T | T | T | T |
| PonSSII | C | C | C | C | C | C | C |
| PonR | C | C | C | C | C | C | C |

Reactions were designated as co-growth (C), taking over (T), or by the diameter of inhibition zones measured in millimeters.

EXAMPLE 5

Field Pot Test Data

The six suppressive isolates, 15, 17, 26, 32, 44, and 93, based on the antibiotic assays against seven virulent isolates, and isolates PonSSII and PonR were field pot tested for scab disease control at Becker, Minn. The suppressive isolates were grown in a metal tray with vermiculite (3500 ml) plus oatmeal broth (900 ml) for 4 weeks, and then mixed with scab-conducive soil at levels of 1%, 5% and 10% (v:v). Treatments of 1% noninoculated vermiculite plus oatmeal broth (V:V) and nonamended scab-conducive soil were used as controls. The potato cultivar Norchip was used and the numbers of Type III, IV, and V lesions per tuber were recorded. A randomized complete block design was used with seven replicates.

The suppressive isolates 17, 15, 32, 44, 93, PonR and PonSSII significantly reduced the number of scab lesions per tuber when compared with control 2, the nonamended disease-conducive soil, and with the 1% level control. The treatment using suppressive isolate 26 was not significantly different from the 1% check at p=0.05. There were no significant differences between suppressive isolates 17, 26, PonSSII and the 1% check at p=0.01. None of the treatments which were inoculated with suppressive isolates were significantly different. However, suppressive isolates 15, 32 and 93 allowed fewer scab lesions to be formed and provided better disease control than the other suppressive isolates.

The results of the field pot test for the biocontrol of the potato scab disease by 8 suppressive isolates is shown below in Table IX.

TABLE IX

| Treatment[1] | Lesion Number[2] | P = 0.05 | P = 0.01 |
|---|---|---|---|
| Check 2 | 3.10 | a | A |
| 1% check | 2.56 | ab | AB |
| 1% 26 | 1.49 | bc | ABC |
| 1% PonSSII | 0.92 | c | BC |
| 1% 17 | 0.76 | c | BC |
| 1% PonR | 0.54 | c | C |
| Between | 0.27 | c | C |
| 1% 44 | 0.23 | c | C |
| 1% 32 | 0.16 | c | C |
| 1% 15 | 0.096 | c | C |
| 1% 93 | 0.092 | c | C |

[1]"1%" represents the ratio (v:v) of the vermiculite plus oatmeal broth with or without a suppressive isolated mixed with disease conducive soil.
"Between" refers to the treatment of plants grown between the pots.
"Check 2" is the non-amended scab conducive soil.
[2]Average lesion numbers of types 5, 4, and 3 per tuber from 7 replicates.

EXAMPLE 6

Coinoculation of Suppressive Strains with Virulent Strains

Suppressive isolates 15, 32, 92, PonSSII, and PonR were tested for their ability to suppress virulent isolates RB4, 82, 87, 88, and 89 in greenhouse tests using the leaf bud cutting method according to Lauer, Amer. Potato J., 54:457–464 (1977). Plants of the cultivar Kennebec were grown in the greenhouse in 3-gallon plastic pots containing pasteurized soil. Shortly after flowering, leaf bud cuttings consisting of a leaf, an axillary bud and a short stem section were cut from the mother plant and transferred to clay pots filled with water-saturated, sterile sand. The stem cuttings were submerged to cover the axillary buds. The soil was kept moist and after 2–3 weeks microtubers began to form from the axillary buds. A 500 $\mu$l spore suspension of one of the virulent isolates at $10^7$–$10^8$ spores/ml was inoculated onto a microtuber, and immediately the same amount of a suppressive isolate at the same concentration was inoculated on the same microtuber.

In a second study, an additional treatment consisting of 500 $\mu$l of sterile water was inoculated immediately after inoculation with a virulent isolate on a microtuber to estimate the effects of rinsing off the virulent isolates with a second inoculation.

The results of the test for biocontrol of scab disease on microtubers by coinoculations of virulent isolate RB4 and a suppressive isolate are shown below in Table X.

TABLE X

| Isolate | Lesion Number[1] |
|---|---|
| RB4 | 38.5 |
| PonSSII/RB4 | 6.5 |
| 32/RB4 | 5.5 |
| PonR/RB4 | 5.0 |
| 93/RB4 | 4.5 |
| 15/RB4 | 3.5 |

[1]Means from lesion numbers of two pots with five microtubers in each.

The means of the results of the tests for the ability of the eight suppressive isolates to inhibit scab disease on microtubers in co-inoculation experiments using virulent isolates 82, 87, 88, and 89 are shown below in Table XI.

TABLE XI

| Isolate | Lesion Number[1] |
|---|---|
| Average of 4 virulent isolates | 80.88 |
| PonR | 7.25 |
| PonSSII | 5.13 |
| 32 | 2.63 |
| 93 | 2.00 |
| 15 | 2.00 |

[1]Means of number of lesions per five tubers. A total of 40 microtubers were co-inoculated with each suppressive isolate singly plus virulent isolates 82, 87, 88, and 89. Ten tubers, five per pot, were used to test each virulent: suppressive isolate combination.

All treatments using the suppressive isolates in co-inoculations with the virulent isolates gave highly significant reductions in number of scab lesions when compared to the virulent isolates alone. Further studies in average inhibition of the above-mentioned suppressive isolates on scab formations indicated that suppressive isolates 15 and 93 provided better control of the disease than the other suppressive isolates. Suppressive isolates 93, 15, and 32 significantly reduced the scab disease in microtubers when compared to PonR. There were no significant differences among suppressive isolates PonR, PonSSII, and 44. No significant interactions were noted between virulent and suppressive isolates on scab occurrence or inhibition of disease on microtubers.

EXAMPLE 7

Pathoqenicity Against Other Plant Pathogens

Twenty-eight suppressive isolates were used in antibiotic and co-plating assays against ten other plant pathogens. The antibiotic assay proceeded as follows. Four suppressive isolates were spot-plated (10 $\mu$l at $10^7$–$10^8$ spores per ml), at 4 spots per plate, on R2YE regeneration media and incubated at 30° C. for 3 days (Hopwood, cited supra). The isolates were killed by inverting the plates over 3 mls of chloroform placed in a watch glass, for 1 hour. The watch glasses with excess chloroform were then removed and the plates left with covers ajar for 30 minutes until all of the excess chloroform evaporated. The plates were overlaid with 15 mls of 1% water agar and inoculated with 100 $\mu$l of a test isolate at a concentration of $10^7$–$10^8$ spores per ml. The resulting plates were inverted and incubated at 30° C. for 3–5 days. Two replicate plates were made for each combination. The average diameter of growth inhibition zones were recorded. The results of the antibiotic assay of growth inhibition of suppressive isolates of Streptomyces spp. on 10 plant pathogens is shown below in Table XII.

TABLE XII[1]

| Isolate | Fusarium 185A | Fusarium 103 | Rhizoctonia solani | Rhizoctonia AG3 | Rhizoctonia AG4 | Cylindrocladium floridanum | Clavibacter michiganense subsp. sepedonicum | Phytophthora megasperma pv. glycinea race 1 | V. dahliae | V. albo-atrum |
|---|---|---|---|---|---|---|---|---|---|---|
| 1 | – | – | – | – | – | – | – | – | – | – |
| 2 | – | – | – | – | – | – | – | – | – | – |
| 5 | – | – | – | – | – | – | – | – | – | – |
| 6 | – | – | – | – | – | – | – | – | – | – |
| 7 | – | – | – | – | – | – | – | – | – | – |
| 15 | 15 | 21 | 15 | 20 | 21 | 30 | 29 | 16 | 12 | 25 |
| 17 | – | – | – | – | – | – | 30 | – | – | – |
| 22 | – | – | – | – | – | – | – | – | – | – |
| 24 | – | – | – | – | – | – | – | – | – | – |
| 26 | – | – | – | – | – | – | – | – | – | – |
| 29 | – | – | – | – | – | – | – | – | – | – |
| 31 | – | – | – | – | – | – | – | – | – | – |
| 32 | 11 | 24 | 12 | 23 | 26 | 32 | 37 | 20 | 17 | 25 |
| 33 | – | – | – | – | – | – | – | – | – | – |
| 34 | – | – | – | – | – | – | – | – | – | – |
| 37 | – | – | – | – | – | – | 23 | – | – | – |
| 38 | – | – | – | – | – | – | – | – | – | – |
| 39 | – | – | – | – | – | – | – | – | – | – |
| 44 | – | – | – | – | – | – | – | – | – | – |
| 48 | – | – | – | – | – | – | – | – | – | – |
| 90 | – | – | – | – | – | – | – | – | $37^2$ | + |
| 91 | – | – | – | – | – | – | 15 | – | – | – |
| 92 | – | – | – | – | – | – | 21 | – | – | – |
| 93 | 10 | 23 | 11 | 22 | 25 | 31 | 35 | 20 | 14 | 20 |
| PonSSI | – | – | – | – | – | – | – | – | – | – |
| PonSSII | – | – | – | – | – | – | – | – | – | – |
| PonR | – | – | – | – | – | – | – | – | – | – |
| PonSSR | – | – | – | – | – | – | 28 | – | – | - |

[1]None of the suppressive isolates seemed to inhibit growth of *Erwinia carotovora* pv. *atrospetica*. The pathogen did not grow well on 1% water agar poured on the top of R2YE medium. Inhibition reactions were designated as no reaction (–), growth promotion (+) and average diameter of inhibition zones in millimeters for two replicates.
[2]Inhibition was not complete.

Isolates 15, 32, and 93 showed growth inhibition on all the plant pathogens except for *E. carotovora* pv. *atroseptica*. Isolates 17, 37, 91, and 92 inhibited growth of *Clavibacter michiganense* subsp. *sepedonicum*, but did not inhibit the other pathogens.

Co-plating assays were completed against *Verticillium albo-atrum* and *V. dahliae* according to the following procedure. One hundred μl of a spore suspension of an isolate of the pathogenic isolate at a concentration of $10^7$–$10^8$ spores/ml was spread in a growth medium in a petri plate. Ten μl of a spore suspension of a suppressive isolate at the same concentration was placed in the center of the plate. R2YE media was used with one replicate for each combination. Readings were recorded after 7 days of incubation at 30° C. The results of the co-plating assays showing growth inhibition imposed by suppressive isolates of Streptomyces spp. on *Verticillium dahliae* and *V. albo-atrum* are shown below in Table XIII.

TABLE XIII[1]

| Isolate | V. dahliae Co-Plating | V. albo-atrum Co-Plating |
|---|---|---|
| 1 | 20 | 37 |
| 2 | 17 | 27 |
| 5 | — | — |
| 6 | 11 | 12 |
| 7 | — | — |
| 15 | 12 | 40 |
| 17 | 12 | 11 |
| 22 | — | 25 |
| 24 | 22 | 29 |
| 26 | — | — |
| 29 | — | 12 |
| 31 | — | — |
| 32 | 22 | 37 |
| 33 | — | — |
| 34 | — | 12 |
| 37 | 15 | 11 |
| 38 | — | — |
| 39 | — | 14 |
| 44 | — | — |
| 48 | — | 13 |
| 90 | 28 | 29 |
| 91 | — | 20 |
| 92 | — | 23 |
| 93 | 28 | 38 |
| PonSSI | — | — |
| PonSSII | — | — |
| PonR | — | 12 |
| PonSSR | — | — |

[1]Inhibition zones were measured in mm, or as no reaction (—).

More suppressive isolates produced competitive growth inhibition zones on the two Verticillium pathogens in co-plating assays than in the antibiotic assays. Isolates 15, 32, 93 showed inhibition zones in both assays against both Verticillium species, and larger inhibition zones appeared on co-plating assays than on antibiotic assays.

The following bacteria have been placed on deposit at American Type Culture Collection (ATCC), 12301 Parklawn Drive, Rockville, Md., 20852, under the accession numbers as follows:

Streptomyces spp. strain 15: ATCC No. 55414;

Streptomyces spp. strain 32: ATCC No. 55416;

Streptomyces spp. strain 93: ATCC No. 55415.

EXAMPLE 8

Selection of Suppressive Strains From Soil

Suppressive strains of Streptomyces have been obtained from suppressive soil at Grand Rapids, Minn. and from soil from the Prosser, WA plot that Menzies first reported to be scab-suppressive in 1959 (Menzies, 1959). Soil samples from the Washington plot have been evaluated and have been shown to have a high density of scab-suppressive Streptomyces isolates. The higher pH of the Washington soil provides for the selection of strains that are ecologically complementary to those from the Minnesota soil which has an acid pH (about 5.6 to 6.8). Isolation of suppressive strains from soil of both plots can be done using one of two strategies. In the first, an Andersen sampler (2000 Inc., Salt Lake City, Utah.) has been used to detect Streptomyces isolates that produce antibiotics against pathogenic *S. scabies* and other plant pathogens as described below. As a second strategy for identifying suppressive strains, Streptomyces spp. can be isolated from suppressive soil using standard plating techniques. Random collections of Streptomyces spp. isolated in this manner can be characterized and evaluated for their ability to inhibit pathogenic strains using the antibiotic assay as described for the suppressive isolates obtained from lenticels of tuber surfaces.

The isolation of suppressive strains from soil samples was accomplished using a rapid screening technique employing the Andersen sampler. Briefly, soil samples about 1 μm in diameter were plated onto a lawn of pathogenic *S. scabies* or other pathogens and those samples exhibiting a zone of inhibition of greater than 12 mm and preferably 35 mm or greater were selected and cultured for isolation of individual strains. A 2% water agar plate was inoculated with a lawn of a pathogenic strain of *S. scabies* (strain RB4), *V. dahliae* or *V. albo-atrum*. A measured amount of field soil that has been milled (about 1 μm or less) to a uniform consistency was added to the Andersen sampler. Soil was impacted onto the agar surface through the Andersen sampler by passing a filtered air current over the soil at a speed of 18 1/min. Soil was impacted onto the agar through stage 6 of the sampler; this stage has 400 impaction sites (1 μ diameter) per plate. The plates were incubated at 30° C. for three-four days and those soil samples exhibiting a zone of inhibition of greater than 35 mm were selected and cultured for isolation of individual strains.

Figure 1:
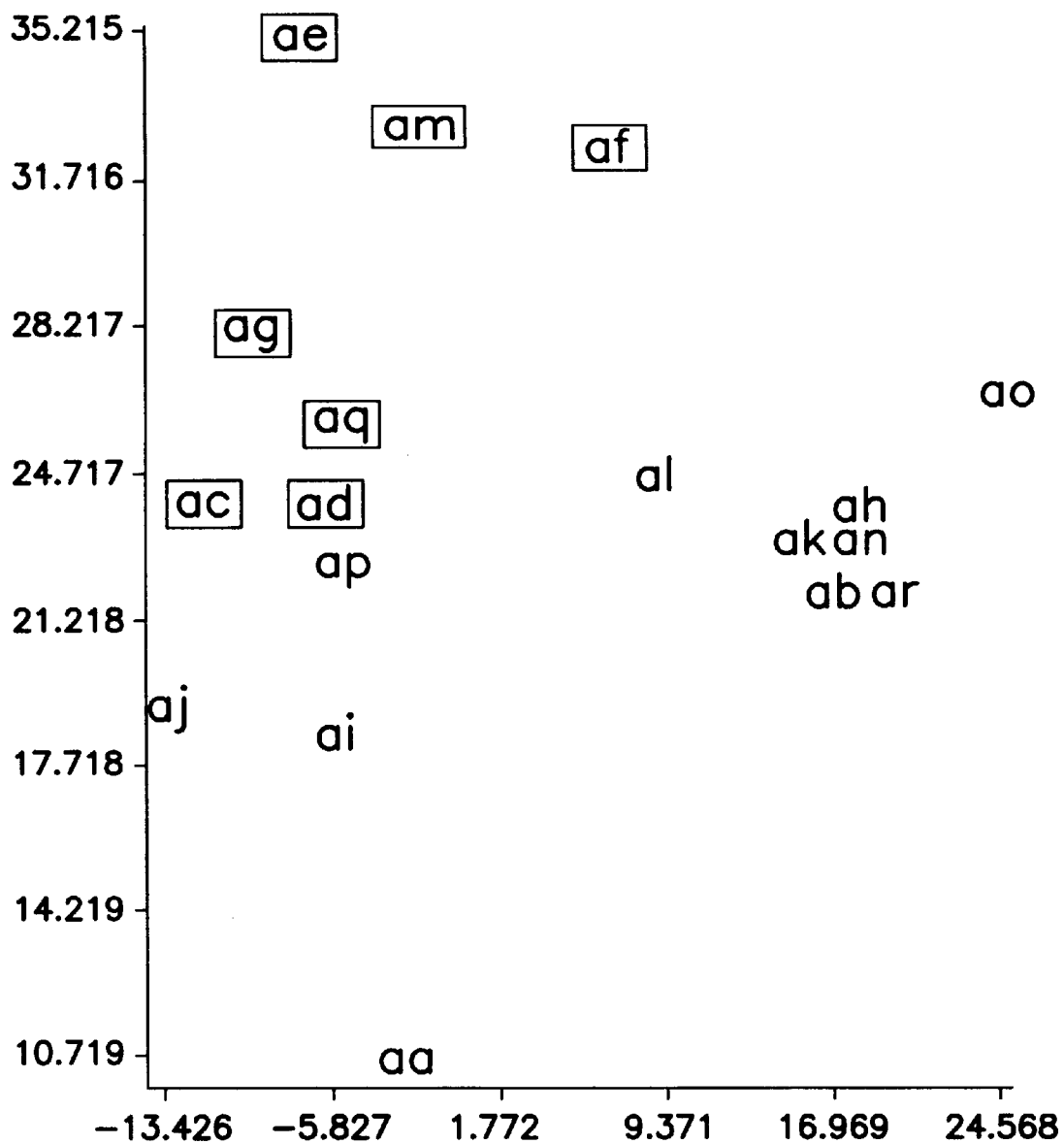
FIG. 1 is principle component analysis of cellular fatty acids of suppressive Streptomyces strains isolated from soil. Each identifier represents a different soil isolate as follows.

Using this method, more than 90 avirulent and suppressive Streptomyces strains were isolated. About 18 suppressive Streptomyces strains including 6 strains from Washington suppressive soil and 12 strains from the Grand Rapids, Minn. suppressive soil were further characterized. These strains are suppressive avirulent Streptomyces spp. that each have a unique cellular fatty acid profile. These suppressive isolates obtained from soil have a fatty acid profile as shown in FIG. 1 as determined according to the method of Example 11. The isolates obtained from suppressive soils had enhanced inhibitory activity as determined by the antibiotic assay as compared with the suppressive isolates obtained from the lenticels of tubers, especially strain 93.

EXAMPLE 9

Isolation of Antibiotics from Suppressive Streptomyces Spp.

Antibiotics produced by different suppressive Streptomyces spp. have been and can be extracted from cultures of the microorganism. Suppressive strain cultures can be and were grown in liquid minimal medium as described previously until they reached early stationary phase of growth as determined by optical density at 650 mm (OD=4–8). Culture medium (about 10 liters) was collected and filtered through Whatman #1 filter paper. The culture filtrate was then further fractionated using chromatographic methods known to those of skill in the art.

Biologically active fractions were identified using a filter disc assay. The filter disc assay allows identification of fractions having biological activity against pathogenic *S. scabies* strain RB4 and other pathogens. Culture filtrate samples were placed on filter paper discs and placed on a freshly seeded lawn of *S. scabies* RB4 on 25 ml of oatmeal agar. The plates were then incubated for 3 days at 25° C. A zone of growth inhibition indicated presence of an inhibitory antibiotic. A zone of inhibition of about 1.8 cm was assigned 1 unit of activity. The inhibitory activity of fractions obtained after subsequent purification can be compared with the zone of inhibition obtained with unfractionated culture filtrate to determine the percent recovery.

The culture filtrate was fractionated using XAD-2 column chromatography (Mallinckrodt.) The column was eluted with increasing concentrations of methanol in water. Fractions were collected starting with 40% methanol. Fractions with biological activity were collected and pooled and 100% of the starting activity was recovered. The biologically active fractions were then run on C18 thin layer chromatography (TLC) in 60% $H_2O$, 40% methanol and 0.3 M NaCl. Bands having biological activity were scraped off and eluted in 60% methanol and 10 mM $KH_2PO_4$ and pooled. Active fractions obtained after thin layer chromatography (TLC) retained 60% of the starting activity. Active fractions were further separated on cellulose TLC and active bands were scraped, eluted and pooled. After cellulose TLC, 30% of the starting activity was recovered. The biologically active fractions were chromatographed by reverse phase HPLC and eluted with a 10 mM $KH_2PO^4$/methanol gradient. Active fractions eluted at 30% methanol as a single peak. Active fractions were pooled and represented 30% of the activity of the starting material. The active material was obtained from a culture filtrate of suppressive strain Streptomyces PonSSII. Similar active material can and will be isolated from culture filtrates of other suppressive strains such as Streptomyces strains 15, 32, and 93.

The antibiotic containing fraction from PonSSII was then characterized for physical characteristics according to standard methods. Digestion of the active fractions with the proteinase K had no effect on the biological activity. Filtration of the biologically active component through a series of size exclusion filters (Amicon) indicated that the size of the antibiotic from PonSSII is less than 3000 mw. The antibiotic fraction was inactivated if pH culture supernatant was increased above pH=7. Antibiotic activity was detected over a pH range of about 4 to 7. The antibiotic containing fractions were also characterized for the ability to directly inhibit growth of different species of bacteria. The results of the testing of different species of microorganisms for inhibition by the antibiotic containing fractions are shown in Table XIV.

TABLE XIV

| Microorganism | Sensitive to Antibiotic from PonSSII |
|---|---|
| *Streptomyces scabies* | + |
| *Staphylococcus aureus* | − |
| *Staphylococcus epidermidis* | − |
| *Streptococcus faecalis* | − |
| *Serratia marcesens* | − |
| *Mycobacterium luteus* | − |
| *Bacillus subtilis* | − |
| *Clostridium perfringins* | − |
| *Escherichia coli* | − |
| *Nocardia asteroides* | − |
| *Streptomyces griseus* | − |
| *Streptomyces venezuela* | − |
| *Actinomyces aneslundii* | − |

EXAMPLE 10

Crop Rotation and Biological Control With Suppressive Streptomyces Strains

Crop rotation is an important strategy for minimizing plant disease and managing soil quality. A biological control strategy will need to be incorporated in to traditional crop management strategies, including crop rotation. Interactions between inoculation of suppressive Streptomyces strains and crop rotation were studied in a multiyear field study at the University of Minnesota Sand Plain Experiment Station.

Plots were inoculated in Year One with a mixture of Streptomyces suppressive strains PonR and PonSSII. In Year One, scab-susceptible potatoes (Red Pontiac) were planted in all plots. In Year Two, soybeans were planted in one-third of the plot, corn was planted in one-third of the plot, and potatoes were planted in the remaining one-third of the plot. In Year Three, all plots were planted with potatoes. In Year Three, the potatoes were evaluated for the number of scab lesions per tuber. The results are shown in FIG. 2. Disease levels were evaluated by determining the mean number of the total 3, 4 and 5 type lesions per tuber.

The results show that disease levels are lowest in plots in which inoculation of the disease suppressive strains has been combined with crop rotation (soybean and corn plots), though the biocontrol agents offer significant disease control even when growing continuous potatoes. The results also show that a single inoculation remains effective into the third growing season. Neither corn nor soybean plants exhibited any negative effects from the presence of the suppressive Streptomyces strains. Thus, a suppressive Streptomyces can provide control of disease if combined with a crop rotation strategy. And, in fact, the combination of using a mixture of suppressive Streptomyces strains in combination with crop rotation may result in an enhancement of control of potato scab and other diseases.

EXAMPLE 11

Identification of Suppressive Strains Using Cellular Fatty Acid Analysis

Gas liquid chromatography of cellular fatty acids can be used to distinguish individual suppressive Streptomyces strains from pathogenic and saprophytic Streptomyces isolates from field soil. The proportion of the total Streptomyces population as represented by the suppressive strain and the population of the rhizosphere can be determined.

Isolates were grown on oatmeal agar at 28° C. for 5–7 days followed by growth in trypticase soy broth for 72 hours. Mycelia were harvested and about 200 mg (wet weight) were processed according to standard methods. Cellular fatty acids were saponified, methylated to form fatty acid methylesters, extracted from the aqueous phase into an organic phase, and washed. The fatty acid methyl esters were separated using a Hewlett Packard 5890A gas chromatograph and peaks were named, measured and expressed as percentages of the total fatty acid profile.

The fatty acid profile of an individual isolate is compared to a library of fatty acid profiles for suppressive strains generated with Microbial Identification Library Generation Software (MIDI, Newark, Del.). Identification and relationship of strains of Streptomyces were determined using cluster (dendrograms) and principle component analysis using the Library Software.

Principal component analysis shows identification of five suppressive Streptomyces strains based on fatty acid composition. Analyses were done using software provided with the Microbial Identification System (MIDI, Inc., Newark). The results are shown in FIG. 3. Each suppressive strain has a unique profile which can be used to identify that strain, including when it is present in a mixed population.

EXAMPLE 12

Persistence of Suppressive Streptomyces In the Soil and Rhizosphere

The persistence of suppressive Streptomyces strains in the rhizosphere and soil was evaluated. The distribution of suppressive Streptomyces spp. strain 93 in the root system of potato plants was determined at a range of inoculum levels. Seed pieces were inoculated with a suppressive strain by dipping them in an inoculum slurry or by incorporating the strain into the soil on a vermiculite base at planting. Roots were sampled at 6, 8 and 10 weeks after planting. At each date, two of the longest roots were taken from each of 4 plants and divided into 10 cm segments. Segments were shaken in sterile water for 1 hours at 40° C. The root washings were serially diluted and plated on amended oatmeal agar. Each root sample was assayed for strain 93, total Streptomyces and total bacteria by dilution plating procedures.

The results show that populations of strain 93 persisted in the rhizosphere for the 10 week period. The population of strain 93 increased over the first 8 weeks and then decreased from 8 to 10 weeks. Populations of strain 93 were found to be evenly distributed across the root system.

The persistence of strain 93 when inoculated with pathogenic strains 82, 85, 87, 89 and RB4 was assessed. A spore suspension of pathogenic strains 82, 85, 87, 89 and RB4 was inoculated in sterile vermiculite and oatmeal broth mix. The pathogenic inoculum was incubated for 4 weeks at room temperature. Pathogen inoculum was mixed with steamed soil in each 12 liter pot at a range of inoculum densities including 0, $3.0 \times 10^7$, $1.5 \times 10^8$ and $3.0 \times 10^8$ cfu/L of soil. Surface sterilized Gemchip seed pieces were planted in the soil. Inoculum of strain 93 was prepared in sterile vermiculite and oatmeal broth mix and incubated for 4 weeks at room temperature. The strain 93 inoculum was spread on soil around seed pieces at $1.0 \times 10^8$ cfu/liter of soil. Plants were grown in the greenhouse for 8 weeks. After 8 weeks, root systems from 3 plants per treatment were sampled.

The results are shown in FIG. 4. The results show strain 93 colonizes the rhizosphere effectively at a wide range of pathogen population densities in the soil.

Persistence of suppressive strains in the soil from year to year was evaluated. Suppressive isolates PonR and PonSSII were introduced into microplots in Year One at 45 ml per tuber using in-furrow application of inoculum. The inoculum was composed of oatmeal broth-vermiculite base. Soil samples were taken about 1, 2 and 3 years later and soil was diluted onto oatmeal agar. Streptomyces colonies were subcultured and stored at 4° C. Identification of Streptomyces was made using cellular fatty acid analysis.

The results show that the suppressive strains effectively colonized the soil. One year after inoculation, the suppressive strains PonSSII and PonR made up approximately 5.4 and 8.7 percent, respectively, of the Streptomyces community in the field plots. Additionally, using cellular fatty acid analyses, the percent of Streptomyces strains that cluster with the pathogenic *S. scabies* was cut in half in plots inoculated with suppressive strains as compared to the non-inoculated plots. SEE TABLE XV.

TABLE XV

| Treatment[1] | % Related to PonSSII[2] | % Related to PonR[2] | % Related to S. scabies[3] | Disease in Biocontrol Plots[4] |
|---|---|---|---|---|
| 1 PonSSII | 5.4 | — | 15.3 | 24.8 a |
| 2 PonR | — | 8.7 | 16.3 | 32.6 ab |
| 3 Control | — | — | 33.3 | 47.1 b |

[1]In-furrow application in year one only of Streptomyces strains PonSSII or PonR grown on an oatmeal-vermiculite base and added at a rate of 45 cc per tuber or the unamended control.

TABLE XV-continued

| Treatment[1] | % Related to PonSSII[2] | % Related to PonR[2] | % Related to S. scabies[3] | Disease in Biocontrol Plots[4] |
|---|---|---|---|---|

[2]Percentage of isolates related to either Streptomyces strains PonSSII or PonR by an Euclidian distance of less than or equal to 12.
[3]Percentage of isolates related to *S. scabies* by an Euclidian distance of less than or equal to 12.
[4]Average number of scab lesions per tuber. Means followed by the same letter are not significantly different at P = 0.10.

These results show that suppressive Streptomyces strains can persist in the rhizosphere and the soil for long time periods (greater than one year) after inoculation.

EXAMPLE 13

Antibodies to Streptomyces Strains 15, 93 and 32

Antibodies to Streptoznyces strains 15, 93 and 32 were prepared using standard methods. Briefly, mycelium and spores collected from pure cultures of Streptomyces strains 15, 93, and 32 were sonicated and each sonicate was combined with Complete Freunds Adjuvant. Each sonicate was injected into rabbits and followed by booster injections at days 2, 3, 7, 8 and 9. After 3 weeks, the antiserum was harvested. The antiserum was tested for the ability to recognize the immunizing strain of Streptomyces by immunofluorescence methods. The results show that each antisera recognized its corresponding immunizing strain of Streptomyces. Cross reaction of the antisera will be analyzed using ELISA.

Monoclonal antibodies can be prepared using standard techniques as described in Harlow & Lane. Briefly, immunization of mammalian host is accomplished by subcutaneous or intraperitoneal injection of the immunogen compound in adjuvant. Administration is repeated periodically and preferably for at least 4 injections.

Three days before the spleen is removed, a priming injection of the immunogen compound is administered. The spleen cells are then harvested and separated. Spleen cells are then fused with an immortal mammal cells, such as mouse myeloma cells, using standard techniques.

Polyethylene glycol or electrical stimulation will initiate fusions. The fused cells are then cultured in wells according to culture techniques known in the art. Cellular secretions in the culture medium are tested after an appropriate time for the presence of the desired monoclonal antibodies. The specificity of the monoclonal antibodies can be identified using an ELISA test and monoclonal antibodies specific for Streptomyces strain 19, 32 or 93 can be identified.

The monoclonal antibodies can be further selected for lack of crossreactivity with other Streptomyces spp. For example, monoclonal antibodies can be identified that do not substantially crossreact with other suppressive Streptomyces spp. or the virulent *S. scabies* strains or other saprophytic Streptomyces strains. The screening assays can be performed by immunoenzymatic assay, immunofluorescence, fluorescence activated cell sorter, radioimmune assay, or immunoprecipitive assay.

EXAMPLE 14

Rolled Towel Assay for Biocontrol Tests of Pythium Seedling Blight of Alfalfa

Pasteurized soil was inoculated with *Pythium ultimum* or *Pythium paroecandrum* and placed on moistened paper towels. The suppressive strains 15, 32 and 93 in the form of spores, granules, or vermiculite inoculum were mixed into soil and alfalfa seed added. The towels were rolled and incubated at 18° C. and 25° C. Controls include soil without the pathogen, soil without the suppressive strain, and soil without pathogen and suppressive strains.

Seedling blight was evaluated by amount of seed rot, root rot, and hypocotyl rot. Good biocontrol was indicated by almost complete germination and decreased rot and hypocotyl rot. Fair biocontrol was indicated by 50% seed rot, and increased root and hypocotyl rot. The results indicate good biocontrol of seedling blight with the suppressive strains at 25° C. and fair-to-good biocontrol at 18° C. The results indicate that cool temperature suppressive strains can and will be selected.

EXAMPLE 15

Identification of Suppressive and Pathogenic Streptomyces Isolates Using Polymerase Chain Reaction Polymerase chain reaction can be used to amplify DNA sequences of a suppressive or pathogenic Streptomyces strain. The PCR products were then separated by agarose gel electrophoresis and stained with ethidium bromide. The pattern of amplified DNA fragments from each isolate is unique and can be used to distinguish suppressive and pathogenic strains.

Polymerase chain reaction was conducted by standard methods as described in Judd et al., Appl. Environ. Microb. 54: 1702 (1993). The primer is complementary to nucleic acid sequences of Streptomyces spp. and was obtained from Dr. J. R. Lupski (Baylor College of Medicine, Houston, Tex.). The primer utilized has the following sequence (SEQ ID NO:1):

5'CTACGGCAAGGCGACGCTGACG 3'

This primer or other primers which are complementary to Streptomyces DNA sequences can be designed based on known nucleic acid sequence information available in the literature. Once the sequence of the primers is selected, they can be prepared by automated DNA synthesis.

Polymerase chain reaction was run with DNA isolated from the following: Streptomyces spp., *S. scabies* strain RB4, *S. scabies* strain 87, S. spp. strain Crystal, *S. scabies* RB5, *S. scabies* Pon C, S. spp. strain 93, *S. scabies* strain PonR, S. spp. strain Pon SSII, S. spp., strain 32, and S. spp. strain 15. The DNA was denatured and annealed to the primer and a PCR reaction was carried out to amplify the DNA between the primer annealing sites. Polymerase chain reaction mixtures include: 62 pmoles primer, 50 ng DNA, 2 units of Taq polymerase, 1.25 mM DNTP mix (1:1:1:1), 10% DMSO, 160 μg/ml BSA and buffer. The buffer is 16.6 mM $(NH_4)_2SO_4$, 67 mM Tris HCl (pH=8.8), 6.7 MM $MgCl_2$, 6.7 μM EDTA and 30 mM B mercaptoethanol. The PCR reaction was run for 35 cycles. PCR products were separated on 1.5% agarose gel and stained with ethidium bromide. Judd et al., *Appl. Environ. Microbiol.*, 59:1702 (1993). The results are shown in FIG. 5.

The results show that each of the suppressive Streptomyces strains had a unique profile of PCR products. This profile of PCR products can be used to confirm the identity of a Streptomyces spp. and to distinguish suppressive and pathogenic strains.

EXAMPLE 16

Generation of Rifampicin Resistant Mutants of Suppressive Streptomyces spp.

Mutants of suppressive Streptomyces spp. can be generated and screened for the ability to produce one or more antibiotics and/or for a selectable marker gene. Spontaneously arising mutants of suppressive Streptomyces spp. were selected.

Single colonies resulting from a dilution series of surviving suppressive strain were grown for 5–7 days on oatmeal agar. Colonies were then selected for rifampicin resistance by growth on oatmeal agar supplemented with 100 μg/ml rifampicin. Colonies that could grow on rifampicin were picked and evaluated for antibiotic production against a virulent strain of Streptomyces as described in Example 2. Mutant suppressive Streptomyces spp. resistant to rifampicin and producing antibiotic inhibitory to at least one pathogenic strain of *S. scabies* were selected. Optionally, the mutants can also be selected for the ability to outgrow pathogenic *S. scabies* and/or to cogrow with other suppressive Streptomyces spp. These strains are useful as biocontrol agents that can be readily detected and distinguished from other soil-born Streptomyces spp. by the presence of an identifiable marker gene such as rifampicin resistance.

EXAMPLE 17

Biocontrol Tests for Septoria Leaf Spot of Hybrid Poplars

An assay procedure has been developed to screen hybrid poplars for leaf spot resistance to *Septoria musiva*. Ostry et al., *Plant Dis.*, 72:497–499 (1988). Hybrid Populus clones were grown in the greenhouse and expanded leaves (3rd or 4th from apex) were collected. Leaves were rinsed with distilled water and 18-mm diameter disks were removed from the leaves placed abaxial surface up in wells of the same size cut in 2% water agar in petri plates. A conidial suspension of *S. musiva* (10 μl at $10^6$/ml) was inoculated onto each disk. The area of leaf necrosis was determined 4–21 days after inoculation and the clones classified as having high, moderate or low resistance to *S. musiva*.

Antibiotic tests indicated that suppressive strains 15, 32 and 93 (plus other strains) produced antibiotics lethal to *S. musiva*. These suppressive strains were applied individually (10 μl at $10^8$ spores/ml) to each leaf disk:

a. Septoria and suppressive strain inoculated the same day;

b. Septoria inoculated to leaf disk 1, 4, 7 days before suppressive strain; and c. The suppressive strain added to leaf disk 1, 4, 7 days before Septoria.

The results shows that good control of the Septoria disease on the leaf disk tissue was obtained if the suppressive strain was pre- or co-inoculated with the Septoria pathogen. The suppressive strain can also be used to control canker of hybrid poplars associated with *Septoria musiva*.

All publications and patent applications in this specification are indicative of the level of skill in the art to which this invention pertains. All publications and patent applications are herein incorporated by reference to the same extent as if each individual publication or patent application was specifically and individually indicated by reference.

What is claimed is:

1. A method for controlling scab disease, comprising:

applying to a crop an effective amount of a suppressive avirulent strain of Streptomyces spp. to inhibit the growth of a virulent pathogenic strain of *Streptomyces scabies*;

wherein the suppressive avirulent strain is selected from the group consisting of Streptomyces strain 15 (ATCC No. 55414), Streptomyces strain 32 (ATCC No. 55416), Streptomyces strain 93 (ATCC No. 55415), and mixtures thereof.

2. The method according to claim 1, wherein the crop is a vegetable selected from the group consisting of potatoes, beets, radishes, carrots, rutabagas, parsnips, turnips, and any combination thereof.

3. The method according to claim 1, wherein the suppressive avirulent strain is applied to the crop in the form of a liquid composition containing about $10^4$–$10^{10}$ CFU of the suppressive avirulent strain per ml, or in the form of a solid composition containing about $10^5$–$10^{12}$ CFU of the suppressive strain per gram.

4. The method according to claim 1, wherein scab lesions on the crop are substantially reduced.

5. A method for inhibiting scab disease comprising:

applying to a crop an effective amount of a combination of at least two suppressive avirulent strains of Streptomyces spp. to inhibit the growth of a virulent strain of *Streptomyces scabies* on the crop, the suppressive avirulent strains being compatible with each other in combination, wherein at least one of the suppressive avirulent strains is selected from the group consisting of Streptomyces strain 15 (ATCC No. 55414), Streptomyces strain 32 (ATCC No. 55416), (ATCC No. 55416), and Streptomyces strain 93 (ATCC No. 55415).

6. A biopesticidal composition comprising, in admixture:

a suppressive avirulent strain of Streptomyces spp. having all the identifying characteristics of Streptomyces spp. strain 15 (ATCC No. 55414); and a carrier.

7. A biopesticidal composition comprising, in admixture:

a suppressive avirulent strain of Streptomyces spp. having all the identifying characteristics of Streptomyces spp. strain 32 (ATCC No. 55416); and a carrier.

8. A biopesticidal composition comprising, in admixture:

a suppressive avirulent strain of Streptomyces spp. having all the identifying characteristics of Streptomyces spp. strain 93 (ATCC No. 55415); and a carrier.

9. The composition of claim 6, wherein said suppressive avirulent strain inhibits growth of one or more plant pathogens selected from *Fusarium solani, Rhizoctonia solani Cylindrocladium floridanum, Clavibacter michiganese* subsp. Sepedonicum, *Phyto megasperma* pv. Glycinea race1, *Verticillium dahliae* and *Verticillium albo-atrum* in an antibiotic assay.

10. The composition of claim 7, wherein said suppressive avirulent strain inhibits growth in an antibiotic assay of one or more plant pathogens selected from *Fusarium solani, Rhizoctonia solani, Cylindrocladium floridanum, Clalibacter michiganese* subsp. Sepedonicum, *Phyto megaperma* pv. Glycinea race1, *Verticallium dahliae* and *Verticillium albo-atrum*.

11. The composition of claim 8, wherein said suppressive avirulent strain inhibits growth in an antibiotic assay of one or more plant pathogens selected from *Fusarium solani, Rhizoctonia solani Cylindrocladium floridanum, Clavibacter michiganese* subsp. Sepedonicum, *Phyto megasperma* pv. Glycinea race1, *Verticillium dahliae* and *Verticillium albo-atrum*.

12. A biopesticidal composition comprising, in admixture: suppressive avirulent strain Streptomyces spp.strain 15 (ATCC No. 55414), and a carrier.

13. A biopesticidal composition comprising, in admixture: suppressive avirulent strain Streptomyces spp.strain 32 (ATCC No. 55416), and a carrier.

14. A biopesticidal composition comprising, in admixture: suppressive avirulent strain Streptomyces spp.strain 93 (ATCC No. 55415), and a carrier.

* * * * *

UNITED STATES PATENT AND TRADEMARK OFFICE
CERTIFICATE OF CORRECTION

PATENT NO. : 6,074,638
DATED : June 13, 2000
INVENTOR(S) : Anderson et al.

It is certified that error appears in the above-identified patent and that said Letters Patent is hereby corrected as shown below:

Column 15,
Line 59, Table I: "$GR^{(2),MN}$" should read -- $GR^{(2),}MN$ --

Column 20,
Table IV, Under Column "26", third row from the bottom "+" should read -- - --

Column 22,
Line 66, "15" should read -- 15 --

Column 29,
Line 24, "$KH_2PO^4$" should read -- $KH_2PO_4$ --

Signed and Sealed this

Thirtieth Day of October, 2001

Attest:

NICHOLAS P. GODICI
Attesting Officer   Acting Director of the United States Patent and Trademark Office

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO:1:

CTACGGCAAG GCGACGCTGA CG                                                    22